United States Patent
Pentlehner et al.

(10) Patent No.: US 10,581,001 B2
(45) Date of Patent: Mar. 3, 2020

(54) ORGANIC ELECTRONIC COMPONENT HAVING A CHARGE CARRIER GENERATION LAYER AND THE USE OF A ZINC COMPLEX AS A P-TYPE DOPANT IN CHARGE CARRIER GENERATION LAYERS

(71) Applicant: OSRAM OLED GmbH, Regensburg (DE)

(72) Inventors: Dominik Pentlehner, Burghausen (DE); Guenter Schmid, Hemhofen (DE); Anna Maltenberger, Leutenbach (DE); Sébastien Pecqueur, La Couture (FR); Florian Kessler, Hoechstadt (DE); Stefan Regensburger, Neumarkt (DE)

(73) Assignee: OSRAM OLED GMBH, Regensburg (DE)

( * ) Notice: Subject to any disclaimer, the term of this patent is extended or adjusted under 35 U.S.C. 154(b) by 0 days.

(21) Appl. No.: 15/763,068

(22) PCT Filed: Sep. 27, 2016

(86) PCT No.: PCT/EP2016/072999
§ 371 (c)(1),
(2) Date: Mar. 23, 2018

(87) PCT Pub. No.: WO2017/055283
PCT Pub. Date: Apr. 6, 2017

(65) Prior Publication Data
US 2018/0277778 A1    Sep. 27, 2018

(30) Foreign Application Priority Data
Sep. 28, 2015   (DE) .................. 10 2015 116 389

(51) Int. Cl.
*H01L 51/00*    (2006.01)
*C07F 3/06*    (2006.01)
(Continued)

(52) U.S. Cl.
CPC ............ *H01L 51/0092* (2013.01); *C07F 3/06* (2013.01); *H01L 51/5278* (2013.01);
(Continued)

(58) Field of Classification Search
None
See application file for complete search history.

(56) References Cited

U.S. PATENT DOCUMENTS

| 5,247,226 A | 9/1993 | Sato et al. |
| 7,575,838 B2 | 8/2009 | Wu et al. |

(Continued)

FOREIGN PATENT DOCUMENTS

| DE | 102012204327 A1 | 9/2013 |
| DE | 102013107113 A1 | 1/2015 |

(Continued)

OTHER PUBLICATIONS

Y. Chen et al.: "High Power Efficiency . . . " Applied Physics Letters, Bd. 98, No. 24, Jun. 17, 2011, pp. 243309-1-243309-3.
(Continued)

*Primary Examiner* — Katie L. Hammer
(74) *Attorney, Agent, or Firm* — McDermott Will & Emery LLP

(57) ABSTRACT

The invention relates to an organic electronic component (100) comprising at least one charge generation layer (5) which has an organically p-doped region (5a) that contains a zinc complex as a p-dopant, said zinc complex in turn containing at least one ligand L of the following structure: formula (I) wherein R1 and R2 can be oxygen, sulphur,
(Continued)

selenium, NH or NR4 independently from one another, wherein R4 is selected from the group containing alkyl or aryl and which can be bonded to R3; and wherein R3 is selected from the group containing alkyl, long-chain alkyl, cycloalkyl, halogen alkyl, at least partially halogenated long-chain alkyl, halogen cycloalkyl, aryl, arylene, halogen aryl, heteroaryl, heteroarylene, heterocyclic alkylene, heterocycloalkyl, halogen heteroaryl, alkenyl, halogen alkenyl, alkynyl, halogen alkynyl, ketoaryl, halogen ketoaryl, ketoheteroaryl, ketoalkyl, halogen ketoalkyl, ketoalkenyl, halogen ketoalkenyl, halogen alkyl aryl, and halogen alkyl heteroaryl, wherein, for suitable groups, one or a number of non-adjacent CH2 groups can be replaced by —O—, —S—, —NH—, —NR°°°—, —SiR°R°°—, —CO—, —COO—, —COR°OR°°—, —OCO—, —OCO—O—, —SO2-, —S—CO—, —CO—S—, —O—CS—, —CS—O—, —CY1=CY2 or —C≡C— independently from one another, and in such a way that O and/or S atoms are not directly bonded to one another, and are replaced optionally with aryl- or heteroaryl preferably containing between 1 and 30 C atoms (terminal CH3 groups are understood to be CH2 groups in the sense of CH2-H). The invention further relates to the use of a zinc complex as a p-dopant in charge generation layers.

20 Claims, 9 Drawing Sheets

(51) Int. Cl.
*H01L 33/14* (2010.01)
*H01L 51/52* (2006.01)
*H01L 51/50* (2006.01)

(52) U.S. Cl.
CPC ........ *H01L 51/5004* (2013.01); *H01L 51/506* (2013.01); *H01L 51/5076* (2013.01); *H01L 2251/552* (2013.01)

(56) References Cited

U.S. PATENT DOCUMENTS

| | | | | |
|---|---|---|---|---|
| 8,808,878 | B2* | 8/2014 | Hou | C07D 277/66 252/301.16 |
| 8,841,153 | B2* | 9/2014 | Goeoetz | H01L 51/001 257/40 |
| 2007/0082284 | A1* | 4/2007 | Stoessel | C07D 213/26 430/84 |
| 2010/0213824 | A1* | 8/2010 | Adler | C07F 15/0033 313/504 |
| 2012/0193619 | A1 | 8/2012 | Taka et al. | |
| 2013/0134410 | A1* | 5/2013 | Kim | H01L 51/0039 257/40 |
| 2015/0221879 | A1* | 8/2015 | Inoue | C07F 15/0033 257/40 |
| 2017/0301872 | A1* | 10/2017 | Schmid | H01L 51/009 |

FOREIGN PATENT DOCUMENTS

| | | |
|---|---|---|
| DE | 102013017361 A1 | 4/2015 |
| DE | 102014114224 A1 | 3/2016 |
| EP | 2605621 A1 | 6/2013 |
| GB | 2508092 A | 5/2014 |

OTHER PUBLICATIONS

Y. Zhang et al.: "The characterization of . . . " Applied Physics a Materials Science & Processing, Bd. 106, No. 3, Nov. 30, 2011, pp. 709-715.

\* cited by examiner

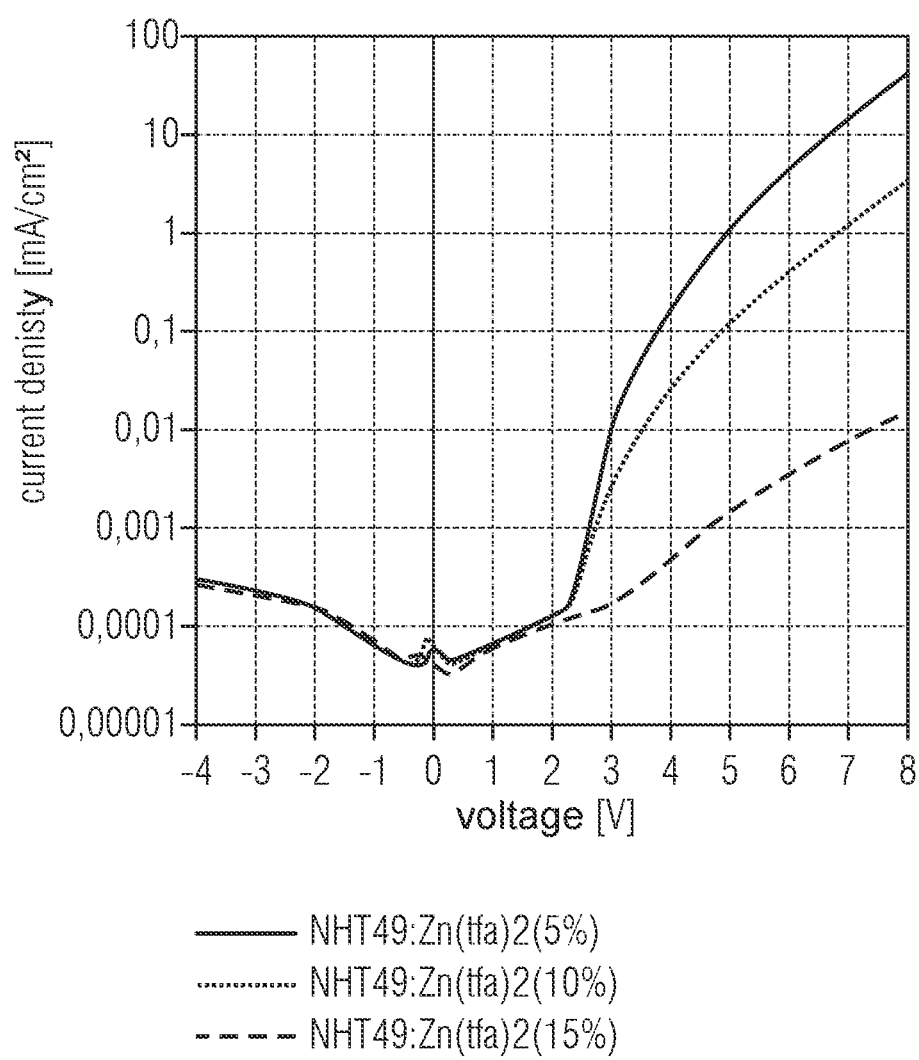

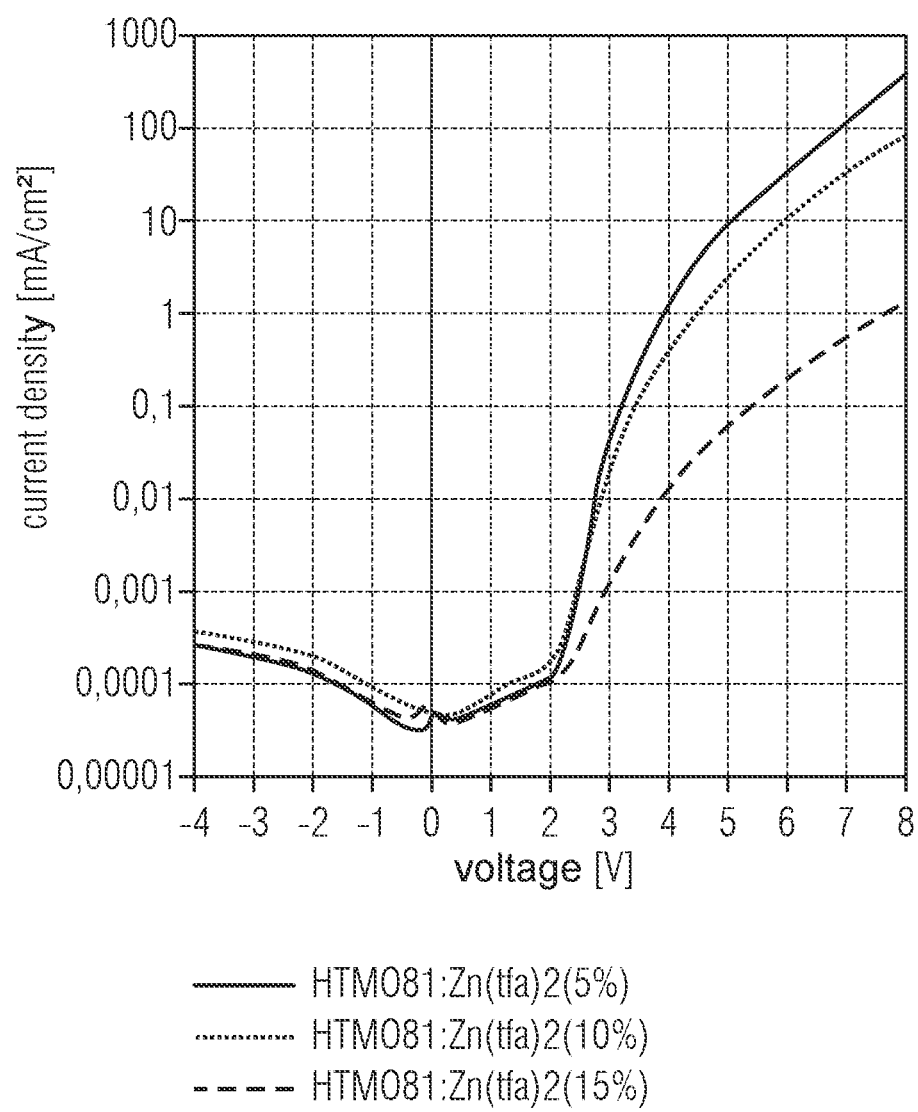

ORGANIC ELECTRONIC COMPONENT HAVING A CHARGE CARRIER GENERATION LAYER AND THE USE OF A ZINC COMPLEX AS A P-TYPE DOPANT IN CHARGE CARRIER GENERATION LAYERS

CROSS-REFERENCE TO RELATED APPLICATIONS

This application is the U.S. National phase under 35 U.S.C. § 371 of International Patent Application No. PCT/EP2016/072999, filed Sep. 27, 2016, which in turn claims the priority of German patent application DE 10 2015 116 389. 6, filed Sep. 28, 2015, the disclosure content of which is hereby incorporated by reference.

DESCRIPTION

The invention relates to the use of zinc complexes as p-dopants in charge carrier generation layers.

Charge carrier generation layers are also referred to as "CGLs" for short. They are of great importance in the field of organic electronics and can be used in various types of components, such as, for example, in organic diodes or organic field-effect transistors. Frequently, they are used in components for converting electric current into electromagnetic radiation.

Powerful organic electronic components require charge carrier generation layers, which allow a good charge carrier separation and an efficient transport of the charge carriers to the layers adjoining the charge carrier generation layer.

In order to fulfil these tasks, powerful p-type dopants are required.

It is therefore an object of the invention to provide materials which are suitable for being used as p-type dopants in charge carrier generation layers of organic electronic components, in particular p-type dopants which allow good conductivity and efficient charge carrier separation in the charge carrier generation layer.

This object is achieved by an organic electronic component according to claim 1.

Accordingly, the invention relates to an organic electronic component having at least one charge carrier generation layer which has an organic p-doped region, which contains a zinc complex as a p-doping agent, wherein the zinc complex contains at least one ligand L of the following structure:

wherein $R^1$ and $R^2$ can be, independently of one another, oxygen, sulfur, selenium, NH or $NR^4$, wherein $R^4$ is selected from the group consisting of alkyl or aryl and can be connected to $R^3$; and $R^3$ is selected from the group consisting of alkyl, long-chain alkyl, cycloalkyl, haloalkyl, at least partially halogenated long-chain alkyl, halocycloalkyl, aryl, arylenes, haloaryl, heteroaryl, heteroarylenes, heterocycloalkylenes, heterocycloalkyl, halogen-heteroaryl, alkenyl, haloalkenyl, alkinyl, haloalkinyl, ketoaryl, haloketoaryl, ketoheteroaryl, ketoalkyl, haloketoalkyl, ketoalkenyl, haloketoalkenyl, haloalkylaryl, haloalkyl heteroaryl, wherein, in the case of suitable residues, one or more non-adjacent $CH_2$ groups can be replaced independently of one another by —O—, —S—, —NH—, $—NR^{\circ\circ\circ}—$, $—SiR^{\circ}R^{\circ\circ}—$, —CO—, —COO—, $—COR^{\circ}OR^{\circ\circ}—$, —OCO—, —OCO—O—, $—SO_2—$, —S—CO—, —CO—S—, —O—CS—, —CS—O—, —CY1=CY2 or —C≡C— in such a way that O and/or S atoms are not directly connected to one another, likewise optionally substituted with aryl or heteroaryl, preferably containing 1 to 30 C atoms (terminal $CH_3$ groups are understood as $CH_2$ groups in the sense of $CH_2$—H).

$R^{\circ}$, $R^{\circ\circ}$, Y1 and Y2 can, for example, each be selected independently of one another from the group consisting of hydrogen, alkyl or aryl. $R^{\circ\circ\circ}$ can be selected, for example, from the group consisting of alkyl and aryl.

The organic electronic component can be, for example, an organic diode, an organic field-, or bipolar transistor or an organic solar cell or organic electrochemical cell.

The electronic component can also be an organic electronic component which converts electrical current into electromagnetic radiation.

In the following, the term "charge carrier generation layer" is to be explained first.

Organic light-emitting diodes (OLEDs) represent an example of such components. In OLEDs, electrons are generated by a cathode (as negative charge carriers) and from the side of the anode "holes" (as positive charge carriers) and recombine in the region of an intermediate emitter layer. In this case, photons, and thus electromagnetic radiation, are emitted. By using charge carrier generation layers, it is possible, for example, to stack two or more such organic light-emitting diodes one above the other and to connect them to one another in series. For this purpose, a charge carrier generation layer is arranged between two OLEDs in each case. An organic electronic component formed in this way is often referred to as a tandem OLED and can have two or more OLED units stacked one above the other. In this case, the charge carrier generation layer functions as a supplier of positive and negative charges for the OLEDs connected thereto. It thus takes over the function of an inner cathode for the one OLED and an inner anode for the other OLED within the organic electronic component, as a result of which the series circuit of the OLEDs arranged one above the other is made possible.

This principle is not restricted to OLEDs arranged one above the other, but is generally valid for organic electronic components. Charge carrier generation layers can serve as charge carrier suppliers within organic electronic components according to the invention, wherein the one side of the charge carrier generation layer provides positive charge carriers and the opposite side of the layer provides negative charge carriers.

This is where charge carrier generation layers have got their names from, namely that charge carrier pairs of positive and negative charge carriers are formed in said layers and are separated from one another. This is carried out at a so-called p-n junction (in the English language called as a "p-n-heterojunction"). For this purpose, charge carrier generation layers have a hole-transporting region and an electron-transporting region. The hole-transporting region of components according to the invention has said zinc complex as a p-type dopant and can therefore be referred to as a p-doped region. The electron-conducting region can be referred to as an n-conducting region. For example, the p-doped region and the n-conducting region can have a common interface and are in contact with one another. For example, however, an intermediate region can also be located between the p-doped region and the n-conducting region. The p-doped region generally has an energetically high LUMO ("lowest unoccupied molecular orbital", i.e. lowest unoccupied molecule) and an energetically high HOMO ("highest occupied molecular orbital"). The energy of LUMO and HOMO in the adjoining n-conducting region, on the other hand, is generally comparatively low. For example when applying an external voltage, an electron can tunnel from the HOMO of the p-doped region into the LUMO of the n-conducting region. This is also possible if there is still an intermediate region which then forms an additional tunnel barrier. The tunneling results in the separation of a charge carrier pair. In the p-doped region, a positive charge is obtained in the n-conducting region. The positive charge is thereupon transported through the p-doped region under the influence of the applied electric field. The negative charge is transported analogously through the n-conducting region.

In addition to the charge carrier generation layer, the organic electronic component according to the invention can have a cathode and an anode, wherein the charge carrier generation layer is arranged between the cathode and the anode. Furthermore, the component can have additional layers between the cathode and the anode, as are usual in conventional organic electronic components.

The organic p-doped region of the charge carrier generation layer has the zinc complex according to the invention as a p-dopant. The organic p-doped region can additionally have a matrix material, for example. In particular, it is possible for the organic p-doped region to have at the same time a matrix material and the p-type dopant, wherein the p-type dopant can be embedded in the matrix material. For example, the p-type dopant can be present homogeneously, that is to say distributed uniformly in the matrix material.

The inventors of the present invention have been found that the zinc complexes according to the invention are surprisingly suitable as p-type dopants in charge carrier generation layers. In contrast, up to now no p-doping substances based on lewis-acidic metal complexes have been known which at the same time also fulfil all the other necessary preconditions for being used in charge carrier generation layers such as suitable processability, stability of the doped layers and sufficiently low absorption. In addition, the use of zinc complexes as a dopant for charge carrier generation layers has not been known. It is therefore all the more surprising that the zinc complexes according to the invention, which are lewis acids, meet all the necessary requirements for being used in charge carrier generation layers.

Thus, the inventors have observed that the p-type dopants according to the invention have very good conductivities on account of their good p-dopant strength, in particular hole conductivities in organic p-doped regions. Matrix materials doped with the zinc complexes exhibit excellent conductivities, such as are required for use in hole injection or hole transport layer-based organic electronic components. Such good hole transport properties are of central importance for the p-doped region of a charge carrier generation layer. After their formation at the p-n junction, the positive charge carriers are transported through the organic p-doped region and finally injected into the adjoining layers. For this purpose, good hole conductivities of the p-doped region, as are achieved with the zinc complexes according to the invention, are essential.

While a series of metal complexes form suitable p-doping substances, however, there are only very few materials which satisfy the second central requirement of p-type dopants in a charge carrier generation layer. In order that charge separation can take place at all, a tunnel current must occur at the p-n junction, that is to say a tunneling of electrons from the HOMO of the p-doped region into the LUMO of the n-conducting region. When using commercially available standard materials for the n-conducting region, the selection of the p-type dopant is decisive for whether or not the charge separation takes place in a sufficiently efficient manner. The reason for this is that the p-type dopant has a decisive influence on the energetic position of the molecular orbitals of the doped region and thus on the relative position of the energy levels involved in the transition. The selection of the p-type dopant is therefore a central aspect for the question of achieving sufficient tunneling currents. If it is possible to generate sufficient tunnel currents, one speaks of the "CGL-effect", that is to say the charge carrier generation layer effect. Only then the preconditions for an efficient charge carrier separation are given.

The inventors of the present invention have found that the zinc complexes according to the invention enable surprisingly high tunneling currents at p-n junctions and thus are suitable for charge carrier generation layers.

Furthermore, the zinc complexes according to the invention have a particularly low absorption in the region of visible light. They are thus characterized by a very good beam permeability and are therefore particularly well suited for being used in optoelectronic components, for examples in light-emitting organic components.

In addition, the zinc complexes according to the invention also have good thermal stability and can be easily vaporized or sublimated. They show a uniform evaporation behaviour during the deposition in layers from the gas phase. They can also be deposited together with a matrix material in a layer without great technical effort, for instance by means of co-evaporation.

The comparatively high stability of the zinc complexes, the decomposition temperature of which is generally significantly above the evaporation temperature thereof, allows simple production of the p-doped region of the charge carrier generation layer by means of gas phase deposition. However, the zinc complexes can also be processed within the framework of a liquid phase deposition. The good stability and volatility simplifies the production of organic electronic components comprising the charge carrier generation layer according to the invention.

Furthermore, the inventors have recognized that the zinc complexes of the described type having the ligands L permit a high variety of complex structures. This diversity can be used in order to adjust the dopant intensity independent of the sublimation temperature during the production.

In addition, the described zinc complexes can be produced without great technical complexity and the starting materials are available inexpensively.

In the following, reference is made to some definitions of terms:

In the context of the present invention, the term "hydrogen" is not limited to hydrogen ($^1$H) alone, but in particular also includes all further isotopes of hydrogen, in particular deuterium ($^2$H or D).

Within the meaning of the present invention, the term "p-dopant" means, in particular, materials which have a lewis acidity and/or are capable complexes with a matrix material in which these materials (albeit only formally) act as lewis azides.

Such a zinc complex matrix material (hole conductor) can have the following structure, for example:

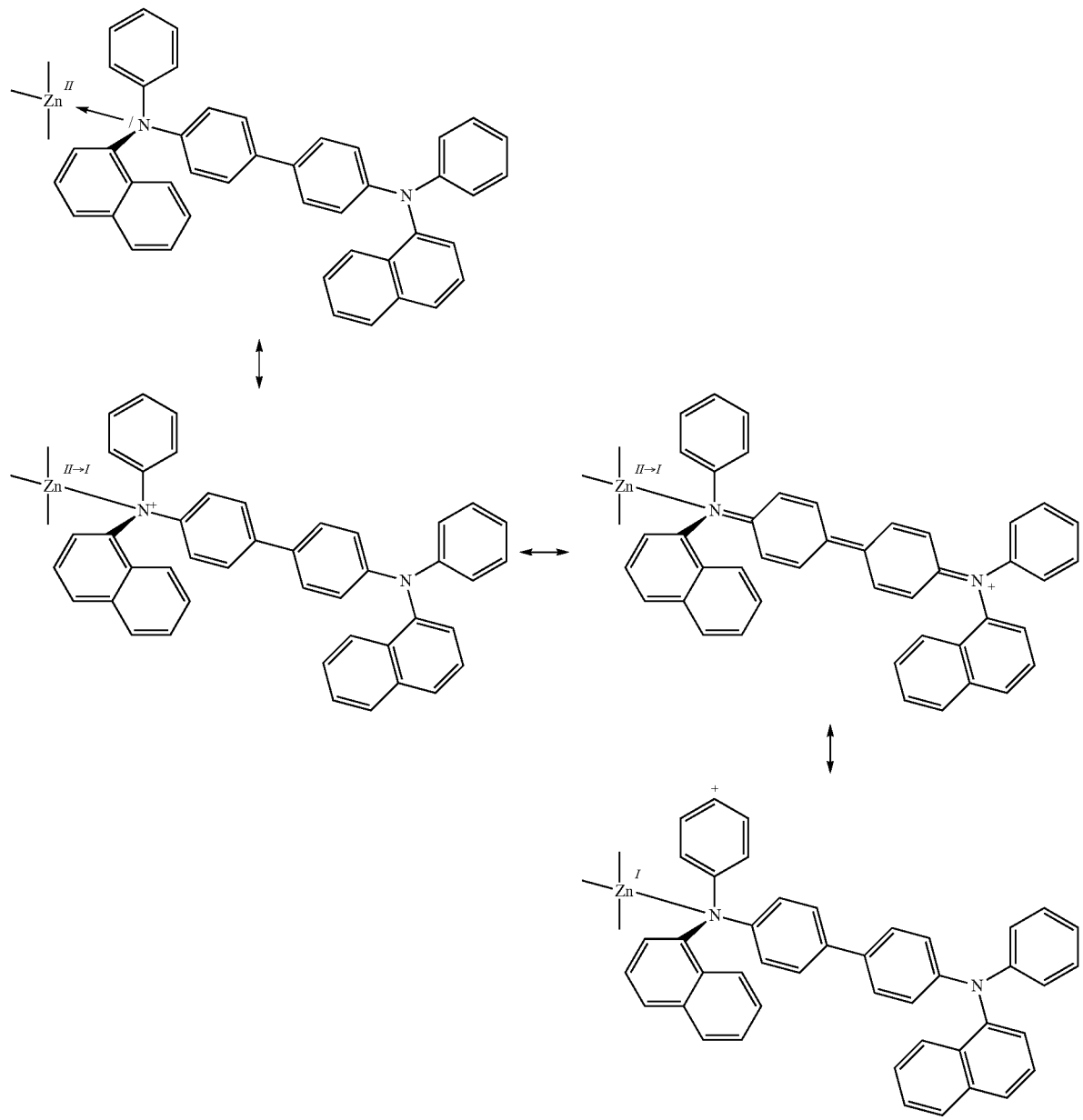

In this case, by way of example, the hole generation and the delocalization of the positive charge are shown using NPB (N,N'-Bis(naphthalen-1-yl)-N,N'-bis(phenyl)-benzidine). For the sake of simplicity, only the zinc central atom is shown in the zinc complex. The number of mesomeric boundary structures is much higher than that of the mesomeric boundary structures shown. A representation of all boundary structures has been dispensed with solely for reasons of space.

Charges can pass from one to the next hole-transport molecule via "hopping". However, conductivity paths are helpful for charge transport but not mandatory.

General Group Definition:

Within the description and the claims, general groups, such as, for example, alkyl, haloalkyl, aryl, etc., are claimed and described. Unless otherwise stated, the following groups within the generally described groups are preferably used within the scope of the present invention:

Alkyl: linear and branched C1-C8-alkyl

Haloalkyl: selected from the group consisting of mono-, di-, tri-, poly- and perhalogenated linear and branched C1-C8-alkyl.

Long-chain alkyls: linear and branched C5-C20 alkyls

At least partially halogenated long-chain alkyl: selected from the group consisting of mono, di, tri-, poly- and perhalogenated linear and branched C5-C20-alkyl.

Cycloalkyl: C3-C8-cycloalkyl, in addition adamantyl and decahydro-naphthyl

Halocycloalkyl: selected from the group consisting of mono-, di-, tri-, poly- and perhalogenated C3-C8-cycloalkyl, in addition mono-, di-, tri-, poly- and perhalogenated adamantyl and decahydronaphthyl.

Alkenyl: C2-C6-alkenyl.

Alkylenes: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl.

Aryl: selected from aromatics having a molecular weight below 300 Da.

Arylenes: selected from the group consisting of: 1,2-phenylene; 1,3-phenylene; 1,4-phenylene; 1,2-naphthylene; 1,3-naphtalenylene; 1,4-naphthylene; 2,3-naphthylene; 1-hydroxy-2,3-phenylene; 1-hydroxy-2,4-phenylene; 1-hydroxy-2,5-phenylene; and 1-hydroxy-2,6-phenylene, Heteroaryl: selected from the group consisting of: pyridinyl; pyrimidinyl; pyrazinyl; triazolyl; pyridazinyl; 1,3,5-triazinyl; chinoninyl; isochinoninyl; chinoxalinyl; imidazolyl; pyrazolyl; benzimidazolyl; thiazolyl; oxazolidinyl; pyrrolyl; thiophenyl; carbazolyl; indolyl; and isoindolyl, wherein the heteroaryl can be connected to the compound via each atom in the ring of the selected heteroaryl.

Heteroarylenes: selected from the group consisting of: pyridindiyl; quinolindiyl; pyrazodiyl; pyrazoldiyl; triazolediyl; pyrazindiyl, thiophendiyl; and imidazolediyl, wherein the heteroarylene functions as a bridge in the compound via any atom in the ring of the selected heteroaryls, particular preference: pyridin-2,3-diyl; pyridin-2,4-diyl; pyridin-2,5-diyl; pyridin-2,6-diyl; pyridin-3,4-diyl; pyridin-3,5-diyl; quinolin-2,3-diyl; quinolin-2,4-diyl; quinolin-2,8-diyl; isoquinolin-1,3-diyl; isoquinolin-1,4-diyl; pyrazol-1,3-diyl; pyrazol-3,5-diyl; triazole-3,5-diyl; triazole-1,3-diyl; pyrazin-2,5-diyl; and imidazole-2,4-diyl, thiophen-2,5-diyl, thiophen-3,5-diyl; a-C1-C6-heterocyclo-alkyl, selected from the group consisting of: piperidinyl; piperidine; 1,4-piperazine, tetrahydrothiophene; tetrahydrofuran; 1,4,7-triazacyclononane; 1,4,8,11-tetraazacyclotetradecane; 1,4,7,10,13-pentaazacyclopentadecane; 1,4-diaza-7-thia-cyclononane; 1,4-diaza-7-oxa-cyclononane; 1,4,7,10-tetraazacyclododecane; 1,4-dioxane; 1,4,7-trithia-cyclononane; pyrrolidine; and tetrahydropyran, wherein the heteroaryl can be substituted with the C1-C6-alkyl via each atom in the ring of the selected heteroaryl.

Heterocycloalkylenes: selected from the group consisting of: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13 pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7thia-cyclonon-2,3-ylene; 1,4-diaza-7-thia-cyclonon-6,8-ylene; 1,4-diaza-7-thia-cyclonon-2,2-ylidene; 1,4-diaza-7-oxacyclonon-1,4-ylene; 1,4-diaza-7-oxa-cyclonon-1,2-ylene; 1,4diaza-7-oxa-cyclonon-2,3-ylene; 1,4-diaza-7-oxa-cyclonon-6,8-ylene; 1,4-diaza-7-oxa-cyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and 1,4,7-trithia-cyclonon-2,2-ylidene, Heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl can be connected to the compound via each atom in the ring of the selected heterocycloalkyl.

Amines: the group —N(R)2, wherein each R is independently selected from: hydrogen; C1-C6-alkyl; C1-c6-alkyl-C6H5; and phenyl, wherein, when both R' are C1-C6-alkyl, both R' can form an —NC3 to NC5 heterocyclic ring, wherein the remaining alkyl chain forms an alkyl substituent on the heterocyclic ring Halogen: selected from the group consisting of: F; Cl; Br and I Pseudohalogen: selected from the group consisting of —CN, —SCN, —OCN, N3, —CNO, —SeCN Carboxylate: the group —C(O)OR, wherein R is selected from: hydrogen; C1-C6-alkyl; phenyl; C1-C6-alkyl-C6H5;

Carbonyl: the group —C(O)R, wherein R is selected from: hydrogen; C1-C6-alkyl; phenyl; C1-C6-alkyl-C6H5 and amines selected from the group: —NR'2, wherein each R' is independently selected from: hydrogen; C1-C6-alkyl; C1-C6-alkyl-C6H5; and phenyl, wherein, when both R' are C1-C6-alkyl, both R' can form an —NC3 to NC5 heterocyclic ring, wherein the remaining alkyl chain forms an alkyl substituent on the heterocyclic ring.

Unless stated otherwise, the following groups are more preferred groups within the general group definition:

Alkyl: linear and branched C1-C6-alkyls.

Haloalkyl: selected from the group consisting of mono-, di-, tri-, poly- and perhalogenated linear and branched C1-C6-alkyl, particularly preferably selected from the group consisting of mono-, di-, tri-, poly- and perhalogenated linear and branched C1-C4-alkyl.

Long-chain alkyls: linear and branched C5-C10 alkyls, preferably C6-C8 alkyls.

At least partially halogenated long-chain alkyl: selected from the group consisting of mono-, di-, tri-, poly- and perhalogenated linear and branched C5-C10-alkyl, preferably mono-, di-, tri-, poly- and perhalogenated linear and branched C6-C8-alkyl.

Cycloalkyl: C6-c8-Cycloalkyl.

Halocycloalkyl: selected from the group consisting of mono-, di-, tri-, poly- and perhalogenated C6-C8-cycloalkyl.

Alkenyl: C3-C6-alkenyl.

Alkylenes: selected from the group consisting of: methylene; 1,2-ethylene; 1,3-propylene; butan-2-ol-1,4-diyl; 1,4-butylene; cyclohexane-1,1-diyl; cyclohexane-1,2-diyl; cyclohexan-1,4-diyl; cyclopentane-1,1-diyl; and cyclopentane-1,2-diyl.

Aryl: selected from the group consisting of: phenyl; biphenyl; naphthalenyl; anthracenyl; and phenanthrenyl.

Arylenes: selected from the group consisting of: 1,2-phenylenes; 1,3-phenylenes; 1,4-phenylenes; 1,2-naphthylylenes; 1,4-napthalenes; 2,3-naphthylylenes and 1-hydroxy-2,6-phenylenes.

Heteroaryl: selected from the group consisting of: pyridinyl; pyrimidinyl; chinoninyl; pyrazolyl; triazolyl; isochinoninyl; imidazolyl; and oxazolidinyl, wherein the heteroaryl can be connected to the compound via each atom in the ring of the selected heteroaryl.

Heteroarylenes: selected from the group consisting of: pyridine-2,3-diyl; pyridine-2,4-diyl; pyridine-2,6-diyl; pyridine-3,5-diyl; quinoline-2,3-diyl; quinoline-2,4-diyl; isoquinoline-1,3-diyl; isoquinoline-1,4-diyl; pyrazole-3,5-diyl; and imidazoles-2,4-diyl.

Heterocycloalkyl: selected from the group consisting of:

Pyrrolidinyl; morpholinyl; piperidinyl; piperidinyl; 1,4-piperazinyl; tetrahydrofuranyl; 1,4,7-triazacyclonanyl; 1,4,8,11-tetraazacyclotetradecanyl; 1,4,7,10,13-pentaaza-pentadecanyl; 1,4,7,10-tetraazacyclododecanyl; and piperazinyl, wherein the heteroaryl can be connected to the compound via each atom in the ring of the selected heteroaryl.

Heterocycloalkylenes: selected from the group consisting of: piperidine-2,6-ylene; piperidine-4,4-ylidene; 1,4-piperazine-1,4-ylene; 1,4-piperazine-2,3-ylene; 1,4-piperazine-2,6-ylene; tetrahydrothiophene-2,5-ylene; tetrahydrothiophene-3,4-ylene; tetrahydrofuran-2,5-ylene; tetrahydrofuran-3,4-ylene; pyrrolidine-2,5-ylene; pyrrolidine-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thia-cyclonon-1,4-ylene; 1,4-diaza-7-thia-cyclonon-2,3-ylene; 1,4-diaza-7-thieincyclonon-2,2-ylidene; 1,4-diaza-7-oxa-cyclonon-1,4-ylene; 1,4 diaza-7-oxa-cyclonon-2,3-ylene; 1,4-diaza-7-oxa-cyclonon-2,2-ylidene; 1,4-dioxane-2,6-ylene; 1,4-dioxane-2,2-ylidene; tetrahydropyrane-2,6-ylene; tetrahydropyrane-2,5-ylene; and tetrahydropyrane-2,2-ylidene, a-C1-C6-alkyl-heterocycloalkyl, wherein the heterocycloalkyl is selected from the group consisting of: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and pyrrolidinyl, wherein the heterocycloalkyl can be connected to the compound via each atom in the ring of the selected hetero-cycloalkyl.

Amine: the group —N(R)2, wherein each R is independently selected from: hydrogen; C1-C6-alkyl; and benzyl.

Halogen: selected from the group consisting of: F and Cl, particularly preferably F.

Carboxylate: the group —C(O)OR, wherein R is selected from hydrogen; C1-C6 alkyl; and benzyl.

Carbonyl: the group: —C(O)R, wherein R is selected from: hydrogen; C1-C6-alkyl; benzyl and amines selected from the group: —NR'2, wherein each R' is independently selected from: hydrogen; C1-C6-alkyl; and benzyl.

According to a preferred embodiment of the component, the zinc complex has a ligand L, wherein R3 is selected from the group consisting of haloalkyl, haloaryl, at least partially halogenated long-chain alkyl, halocycloalkyl, halohet-eroaryl, haloalkylaryl and haloalkylheteroaryl, wherein the halogen can be, in particular, fluorine.

Halogens such as fluorine have a strong electron-withdrawing effect on account of their high electronegativity. This is of great importance for adapting the electronic properties of the complex. In particular, the electron-withdrawing groups permit a strengthening of the lewis acidity of the zinc complex and thus its effect as a p-dopant. In addition, electron-withdrawing groups such as halogens and haloalkyls can have a stabilizing effect on the zinc complex according to the invention.

For the above mentioned groups $R^3$ is further preferably:

Perfluoroalkyl having 1 to 8 carbon atoms is particularly preferred as the haloalkyl, further preferably perfluoroalkyl having 1 to 6 carbon atoms and most preferably perfluoroalkyl having 1 to 4 carbon atoms. It is most preferred if $R^3$ represents trifluoromethyl, pentafluoroethyl, heptafluoro-n-propyl or heptafluoro-iso-propyl. Of these, trifluoromethyl is most preferred.

Perfluoroaryl, in particular perfluorophenyl, is particularly preferred as haloaryl. Furthermore, phenyl substituted by one or more $CF_3$ groups is preferred as the haloalkylaryl.

Particularly preferred halocycloalkyl is perfluoroalkyl having 6 to 8 carbon atoms.

According to a preferred embodiment of the invention, $R^3$ is not aromatic. Non-aromatic radicals $R^3$ promote good p-dopant properties and can have favourable properties during processing, for example during gas phase deposition, and have proven to be highly suitable for achieving good tunnel currents.

According to a further preferred embodiment of the invention, $R^3$ is saturated.

According to another development of the invention, $R^3$ is linear.

According to a further, different development of the invention, $R^3$ is branched.

According to a particularly preferred embodiment of the invention, $R^3$ is perfluorinated. Zinc complexes of this type have good p-dopant properties.

Fluorine is well suited as a substituent of the radical $R^3$ on account of its high electronegativity, since the lewis acidity of the complex increases by the electron-attracting properties and thus improves the dopant strength. The higher the fluorine content, the greater this effect.

A preferred embodiment of the organic electronic component according to the invention has zinc complexes, the ligand L of which has a substituent of the following general formula as a radical $R^3$:

*—$(CF_2)$—$CF_3$, wherein n has the values from 0 to 19, preferably from 0 to 7, more preferably 0 to 5, most preferably 0 to 3. Of all radicals, $R^3$=*—$CF_3$.

"*" in each case describes the binding site of the radical $R^3$.

An alternative embodiment relates to an organic electrical component according to the invention having a zinc complex, wherein the radical $R^3$ of the ligand L is selected from the group consisting of:

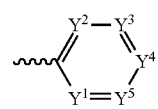

wherein $Y^1$-$Y^5$ are selected independently of one another from the group consisting of C—H, C-D, C—F, C—$NO_2$, C—CN, C-halogen, C-pseudohalogen, N or C—$C_nF_{2n+1}$ where n=1 to 10, in particular C—$CF_3$ (i.e. n=1).

Such zinc complexes are particularly stable and are therefore particularly suitable for use as a p-type dopant.

According to a further embodiment, $R^3$ is selected from the group consisting of:

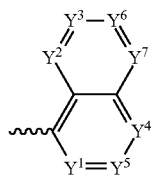

wherein $Y^1$-$Y^7$ are selected independently of one another from the group consisting of C—H, C-D, C—F, C—$NO_2$, C—CN, C-halogen, C-pseudohalogen, N or C—$C_nF_{2n+1}$ where n=1 to 10, in particular C-$CF_3$ (i.e. n=1).

According to a preferred embodiment, $R^3$ is selected from the group consisting of:

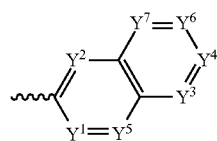

wherein $Y^1$-$Y^7$ are selected independently of one another from the group consisting of C—H, C-D, C—F, C—$NO_2$, C—CN, C-halogen, C-pseudohalogen, N or C—$C_nF_{2n+1}$ where n=1 to 10, in particular C—$CF_3$ (i.e. n=1).

According to a preferred embodiment, $R^3$ is selected from the group consisting of:

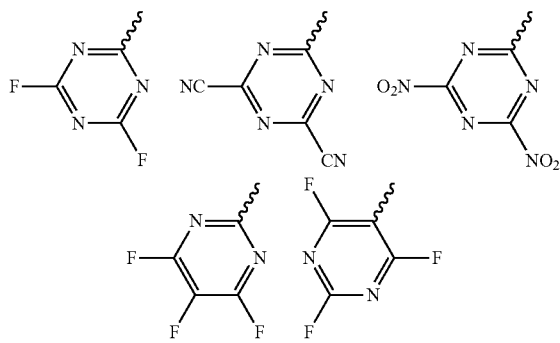

According to another development of the invention, $R^3$ is selected from the group consisting of halogenated, preferably perhalogenated and/or pseudohalogenated pteridines, isopteridines, naphtyridines, quinoxalines, azaquinoxalines.

A particularly preferred embodiment of the invention relates to an organic electrical component according to the invention, in which the two groups $R^1$ and $R^2$ of the ligand L of the zinc complex are in each case oxygen atoms. In this case, the ligand L is a carboxylate ligand.

The inventors of the present invention have recognized that the zinc complexes of the carboxylates represent stable and at the same time particularly effective p-dopants. The carboxylate ligands are also readily available and inexpensive, since the respective associated carboxylic acids are widespread and cost-effective.

In a further preferred embodiment, the metal complex can have at least one ligand L selected from the group of non-substituted, partially fluorinated or perfluorinated organic carboxylic acids.

Organic carboxylic acids can generally be selected from the groups of aliphatic, saturated monocarboxylic acids; aliphatic, unsaturated monocarboxylic acids; aliphatic, saturated dicarboxylic acids; aliphatic, saturated tricarboxylic acids; aliphatic, unsaturated dicarboxylic acids; aromatic carboxylic acids; heterocyclic carboxylic acids; aliphatic, unsaturated, cyclic monocarboxylic acids. Particularly preferred partial or perfluorinated ligands L are selected from substituted or unsubstituted compounds of acetic acid, phenylacetic acid and/or benzoic acid and are listed below by way of example. Non-fluorinated, partially fluorinated or perfluorinated acetic acid is particularly preferred. These ligands are particularly well-suited carboxylate ligands on account of their electron-withdrawing substituents, since they enable particularly high lewis acidity of the zinc complex.

According to a preferred embodiment of the invention, the ligand L is a non-aromatic ligand. These ligands enable good tunnel currents at p-n junctions.

Furthermore, examples of Ligands L which may be mentioned are: fluorinated benzoic acids such as, for example, 2-(Trifluoromethyl) benzoic acid; 3,5-Difluoro benzoic acid; 3-Hydroxy-2,4,6-triiodo benzoic acid; 3-Fluoro-4-methyl benzoic acid; 3-(Trifluoromethoxy) benzoic acid; 4-(Trifluoromethoxy) benzoic acid; 4-Chloro-2,5-difluoro benzoic acid; 2-Chloro-4,5-difluoro benzoic acid; 2,4,5-Trifluoro benzoic acid; 2-Fluoro benzoic acid; 4-Fluoro benzoic acid; 2,3,4-Trifluoro benzoic acid; 2,3,5-Trifluoro benzoic acid; 2,3-Difluoro benzoic acid; 2,4-Bis(trifluoromethyl) benzoic acid; 2,4-Difluoro benzoic acid; 2,5-Difluoro benzoic acid; 2,6-Bis(trifluoromethyl) benzoic acid; 2,6-Difluoro benzoic acid; 2-Chloro-6-fluoro benzoic acid; 2-Fluoro-4-(trifluoromethyl) benzoic acid; 2-Fluoro-5-(trifluoromethyl) benzoic acid; 2-Fluoro-6-(trifluoromethyl) benzoic acid; 3,4,5-Trifluoro benzoic acid; 3,4-Difluoro benzoic acid; 3,5-Bis (trifluoromethyl) benzoic acid; 3-(Trifluoromethyl) benzoic acid; 3-Chloro-4-fluoro benzoic acid; 3-Fluoro-5-(trifluoromethyl) benzoic acid; 3-Fluoro benzoic acid; 4-Fluoro-2-(trifluoromethyl) benzoic acid; 4-Fluoro-3-(trifluoromethyl) benzoic acid; 5-Fluoro-2-methyl benzoic acid; 2-(Trifluoromethoxy) benzoic acid; 2,3,5-Trichloro benzoic acid; 4-(Trifluoromethyl) benzoic acid; Pentafluoro benzoic acid; 2,3,4,5-Tetrafluoro benzoic acid;

fluorinated or non-fluorinated phenylacetic acid such as e.g. 2-Fluoro-phenylacetic acid; 3-Fluoro-phenylacetic acid; 4-Fluoro-phenylacetic acid; 2,3-Difluoro-phenylacetic acid; 2,4-Difluoro-phenylacetic acid; 2,6-Difluoro-phenylacetic acid; 3,4-Difluoro-phenylacetic acid; 3,5-Difluoro-phenylacetic acid; Pentafluoro-phenylacetic acid; 2-Chloro-6-fluoro-phenylacetic acid; 2-Chloro-3,6-difluoro-phenylacetic acid; 3-Chloro-2,6-difluoro-phenylacetic acid; 3-Chloro-4-fluoro-phenylacetic acid; 5-Chloro-2-fluoro-phenylacetic acid; 2,3,4-Trifluoro-phenylacetic acid; 2,3,5-Trifluoro-phenylacetic acid; 2,3,6-Trifluoro-phenylacetic acid; 2,4,5-Trifluoro-phenylacetic acid; 2,4,6-Trifluoro-phenylacetic acid; 3,4,5-Trifluoro-phenylacetic acid; 3-Chloro-2-fluoro-phenylacetic acid; α-Fluoro-phenylacetic acid; 4-Chloro-2-fluoro-phenylacetic acid; 2-Chloro-4-fluoro-phenylacetic acid; α,α-Difluoro-phenylacetic acid;

Ethyl 2,2-Difluoro-2-phenylacetato; and

Fluorinated or non-fluorinated acetic acid such as, for example, methyl-trifluoroacetate; Allyl-trifluoroacetate; Ethyl-trifluoroacetate; Isopropyl-trifluoroacetate; 2,2,2-Trifluoroethyl-trifluoroacetate; Difluoro acetic acid; Trifluoro acetic acid; Methyl-chlorodifluoroacetate; Ethyl-bromodifluoroacetate; Chlorodifluoro acetic acid; Ethyl-chlorofluoroacetate; Ethyl-difluoroacetate; (3-Chlorophenyl)-difluoro acetic acid; (3,5-Difluorophenyl)-difluoro acetic acid; (4-Butylphenyl)difluoro acetic acid; (4-tert-Butylphenyl)difluoro acetic acid; (3,4-Dimethylphenyl)-difluoro acetic acid; (3-Chloro-4-fluorophenyl)-difluoro acetic acid; (4-Chlorophenyl)-difluoro acetic acid; 2-Biphenyl-3',5'-difluoro acetic acid; 3-Biphenyl-3',5'-difluoro acetic acid; 4-Biphenyl-3',5'-difluoro acetic acid; 2-Biphenyl-3',4'-difluoro acetic acid; 3-Biphenyl-3',4'-difluoro acetic acid; 4-Biphenyl-3',4'-difluoro acetic acid and 2,2-Difluoro-propionic acid or higher homologs thereof. If the ligands L have acidic groups, the groups can be deprotonated in a preferred embodiment.

Of said ligands L, the fluorinated acetic acid-based ligands are particularly preferred. They are particularly suitable as p-type dopants for charge carrier generation layers, since they lead to very good tunnel currents at p-n junctions and thus allow a very good charge carrier separation. At the same time, matrix materials are doped with these zinc complexes, exhibit particularly good hole-conductor properties and good electron-blocking properties. Of the mentioned ligands, trifluoro¬acetate ("tfa" for short) is most preferred.

In a preferred embodiment of the invention, the zinc complex is a homoleptic zinc complex, which has only the ligand L and no ligands differing therefrom. For example, it is possible for the zinc complex to have only carboxylate ligands. However, it must be taken into account in each case that the introduction of a zinc complex within a matrix can also be coordinated with the matrix material in addition to a ligand L, e.g. a carboxylate ligand.

In a further embodiment of the invention, the zinc complex is a heteroleptic complex. By using more than only one type of ligand, a greater variety is made possible. In addition, the lewis acidity of the zinc atoms of the complex can be partially controlled in this way, as a result of which effective p-type dopants can be achieved.

An embodiment of the invention relates to a component according to the invention, wherein the zinc complex comprises, in addition to the ligand L, at least one ligand differing therefrom, which is bonded to a zinc central atom of the zinc complex via a bonding atom. The adhesive can, for example, be oxygen. The ligand is then an alcoholate.

Another development of the invention relates to a component according to the invention, wherein the zinc complex comprises, in addition to the ligand L, at least one further ligand $L^C$, which is bound to a zinc central atom via a carbon atom. The zinc complex thus comprises at least one zinc-carbon bond. Zinc complexes of this form enable a particularly pronounced variety of the structure of zinc complexes, which extend further beyond the structures of known p-type dopants with the ligand L.

The at least one further ligand $L^C$ can be, independently of one another, a substituted or unsubstituted, branched or linear, and also a cyclic alkyl. It can likewise be a substituted or unsubstituted aryl or heteroaryl. For example, $L^C$ can be, but is not restricted to, methyl, ethyl, propyl, iso-propyl, butyl, iso-butyl, tert-butyl, pentyl-, hexyl-, phenyl-, benzyl-, naphthyl-, cyclohexyl-, adamantly-, or other typical ligands of known organometallic complexes of zinc as ligand $L^C$.

The inventors have recognized that these complexes have a unique variety in the coordination geometry of the zinc in combination with the previously described ligand L. In particular, the inventors have recognized that these zinc complexes with both types of ligands, L and $L^C$, are surprisingly p-dopants which can be used for doping matrix materials in organic electrical components and can also be used for the charge carrier generation layer. These complexes offer new possibilities with regard to the adaptation of the zinc complexes with regard to the doping strength.

In a preferred embodiment, $L^C$ can be a haloalkyl. Such complexes frequently have a higher lewis acidity. This is particularly the case when the halogen is fluorine.

In a further embodiment, the ligand $L^C$ can comprise at least one fluorine atom. In particular, the at least one ligand $L^C$ can be selected independently of one another from the group of fluorinated, branched or linear and cyclic alkyls. Likewise, $L^C$ can be a fluorinated aryl or heteroaryl. For example, the substituents, but not restricted the invention thereof, like methyl-, ethyl-, propyl-, isopropyl-, butyl-, isobutyl, tert-butyl, pentyl, hexyl, phenyl, benzyl, naphthyl, cyclohexyl, adamantyl or other typical ligands of known organometallic complexes of zinc can act as ligand $L^C$, if these substituents are modified by fluorination, i.e. one or more hydrogen atoms have been replaced by fluorine atoms. For example, the analog perfluorinated substituents can also be used as the ligand $L^C$.

According to a further embodiment, the metal complex is (without the presence of a matrix material) lewis acid, i.e. it acts as an electron pair acceptor. This has proven to be preferred for interaction with matrix materials of the p-doped region of the charge carrier generation layer.

According to another preferred development of the invention, the metal complex (without the presence of a matrix material) has at least one open or partially accessible coordination site. This has also proven to be preferred for interaction with the matrix materials.

A further embodiment of the invention relates to an organic electronic component comprising a zinc complex, wherein zinc can have the coordination numbers 4, 5 and 6. For example, the central zinc atom can be tetrahedrally or octahedrally coordinated. The inventors have recognized that the different types of coordination of the zinc are also useful for the generation of a plurality of p-type dopants based on zinc complexes.

In a particularly preferred embodiment of the invention, zinc has the oxidation state II. Zinc in the oxidation state II has a good lewis acidity and is therefore suitable as a p-type dopant.

According to one embodiment, the zinc complex is a mononuclear complex having a single zinc central atom.

In a different embodiment, the zinc complex is not a mononuclear complex but a polynuclear metal complex. For example, the metal complex can comprise 2, 3, 4, 5, 6 or even more metal atoms.

In another embodiment, the zinc complex is a trinuclear or pentnuclear metal complex. In contrast to other metal complexes with the ligand L, zinc is not restricted to mononuclear, di-, tetra- and hexanuclear complexes, but also enables the formation of polynuclear zinc complexes with an odd number of central atoms. For example, three or even five zinc atoms can be present in the complex. When three zinc atoms are present, they can be present, for example, in a virtually linear arrangement, such that they are bridged by the ligand L, for example. These structures are unique for zinc complexes. The inventors have recognized that the versatility of the zinc complex chemistry enables new flexibility in the doping.

In one embodiment of the invention, at least one ligand L is terminally bonded to a zinc atom. According to a preferred embodiment of the invention, it is possible here, in such a way that at least one ligand L reacts only with one bonding atom, that only one of the two groups $R^1$ or $R^2$ coordinates to the zinc. This can be represented schematically as follows:

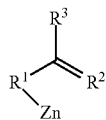

For the example, L is a carboxylate ligand, i.e. a ligand L in which both $R^1$ and $R^2$ are an oxygen atom, that is to say that only one of the two oxygen atoms is bound to the zinc atom.

In another embodiment, the zinc complex comprises at least one ligand L, which is coordinated with both bonding atoms to the same zinc atom. This can be represented schematically as follows:

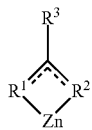

For the example, L is a carboxylate ligand, i.e. a ligand L in which both $R^1$ and $R^2$ are an oxygen atom, that is to say that both oxygen atoms are bound to the zinc atom.

Another development of the invention relates to an organic electrical component, wherein the zinc complex is a polynuclear metal complex and at least one of the ligands L at the same time coordinatively connects two metal atoms.

Without being bound by the theory, the possibility of bridging between the at least two metal atoms with the ligand L of the zinc complex is obtained in the case of polynuclear complexes. In this case, for example, a two- or three-dentate coordination of the metal atom can be carried out. This can be represented schematically as follows:

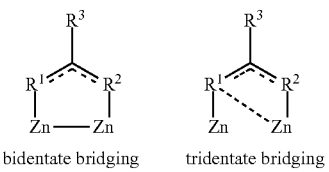

bidentate bridging     tridentate bridging

In another development of the invention, the zinc complex is a polynuclear metal complex comprising at least two ligands L, wherein at least one of the ligands coordinatively connects two metal atoms, while at least one further ligand L is bound terminally to a metal centre of the zinc complex.

In another development of the invention, the zinc complex comprises at least two zinc atoms. The complex can have exactly two zinc atoms, for example, but it can also have three, four, five or six zinc atoms or even more zinc atoms.

The inventors have recognized that more than only one zinc atom offers the advantage, in such a way that corresponding complexes provide a plurality of zinc atoms as lewis acid centres and thus can be particularly effective as as a p-type dopant.

According to one embodiment, the zinc complex has no metals different from zinc.

Another embodiment of the invention relates to an organic electrical component according to the invention, wherein the zinc complex has at least one metal other than zinc in addition to zinc.

If different metal atoms are used to construct a polynuclear complex, a hetero-bimetallic complex is obtained.

Here, too, the ligand L can have a bridging effect, which can be represented schematically as follows:

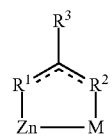

M is a metal atom different from zinc, which forms a further central atom of the zinc complex.

A further embodiment of the invention relates to a component according to the invention as just described, wherein the metal other than zinc is selected from the group comprising Mn, Mg, Ca, Sr, Ba, Cu.

A particularly preferred embodiment of the organic electronic component according to the invention is distinguished by an organic p-doped region, which is an organic p-doped layer. The p-doped layer can in particular be a continuous, area-covering layer.

A preferred embodiment of the organic electronic component according to the invention is distinguished by an organic p-doped region, which has an organic hole-conducting matrix into which the p-type dopant is introduced. In particular, the zinc complex can be homogeneously distributed in the matrix material. For example, the p-doped region can be effected by co-evaporation of the zinc complex and of the material forming the matrix. A particularly homogeneous distribution can thus be achieved.

According to one embodiment, the p-doped region can consist of the p-type dopant and the matrix material.

Materials having good hole transport properties are particularly suitable as matrix materials for the p-doped region of the charge carrier generation layer, which can also be easily processed and can be doped with the zinc complex without great technical effort.

According to a preferred embodiment, the p-doped region of the charge carrier generation layer can be produced in the gas phase and the liquid phase. In the gas phase deposition, both p-type dopant and matrix material are used together, are preferably vaporized from different sources in the high vacuum and deposited as a layer. During processing from the liquid phase, the zinc complex and the matrix material are dissolved in a solvent and deposited by means of printing techniques, spin coating, knife coating, solder coating, etc. The finished layer is obtained by evaporation of the solvent. In this case, any doping ratios can be set by the different mass ratios of metal complex to matrix material.

Particularly preferably, the following hole-conducting matrix materials for the p-doped region of the charge carrier generation layer can be processed by means of a solvent process:

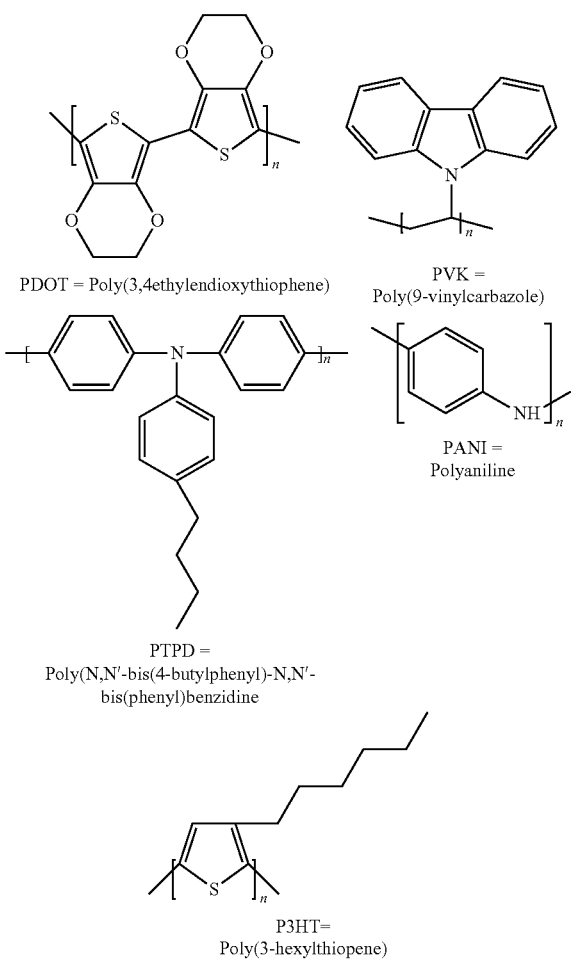

PDOT = Poly(3,4ethylendioxythiophene)

PVK = Poly(9-vinylcarbazole)

PANI = Polyaniline

PTPD = Poly(N,N'-bis(4-butylphenyl)-N,N'-bis(phenyl)benzidine

P3HT = Poly(3-hexylthiopene)

In addition, matrix materials which are referred to as "small molecules" can be particularly preferably processed by means of a solvent process. This substance class is known to the person skilled in the art and includes, for example, Spiro-TAD (2,2',7,7'-Tetrakis-(N,N-diphenylamino)-9,9'-spirobifluorene) and Spiro-TTB (2,2',7,7'-Tetrakis-(N,N'-di-p-methylphenylamino)-9,9'-spirobifluorene and further materials such as those listed in this application as matrix materials.

A particularly preferred embodiment of the organic electronic component according to the invention has an organic p-doped region which has one of the following organic matrix-forming materials with hole-conducting properties:
NPB (N,N'-Bis(naphthalen-1-yl)-N,N'-bis(phenyl)-benzidine),
β-NPB N,N'-Bis(naphthalen-2-yl)-N,N'-bis(phenyl)-benzidine),
TPD (N,N'-Bis(3-methylphenyl)-N,N'-bis(phenyl)-benzidine),
Spiro-TPD (N,N'-Bis(3-methylphenyl)-N,N'-bis(phenyl)-benzidine),
Spiro-NPB (N,N'-Bis(naphthalen-1-yl)-N,N'-bis(phenyl)-spiro),
DMFL-TPD N,N'-Bis(3-methylphenyl)-N,N'-bis(phenyl)-9,9-dimethyl-fluorene),
☐-NPD N,N'-Bis(naphthalen-1-yl)-N,N'-bis(phenyl)-2,2'-dimethylbenzidine,
N,N'-Bis(3-methylphenyl)-N,N'-bis(phenyl)-2,7-diamino-9,9-spirofluorene,
N,N'-Bis(naphthalen-1-yl)-N,N'-bis(phenyl)-2,7-diamino-9,9-spirofluorene,
DMFL-NPB (N,N'-Bis(naphthalen-1-yl)-N,N'-bis(phenyl)-9,9-dimethyl-fluorene),
DPFL-TPD (N,N'-Bis(3-methylphenyl)-N,N'-bis(phenyl)-9,9-diphenyl-fluorene),
DPFL-NPB (N,N'-Bis(naphthalen-1-yl)-N,N'-bis(phenyl)-9,9-diphenyl-fluorene),
Spiro-TAD (2,2',7,7'-Tetrakis(N,N-diphenylamino)-9,9'-spirobifluorene),
9,9-Bis[4-(N,N-bis-biphenyl-4-yl-amino)phenyl]-9H-fluorene,
NPAPF 9,9-Bis[4-(N,N-bis-naphthalen-2-yl-amino)phenyl]-9H-fluorene,
NPBAPF 9,9-bis[4-(N-naphthalen-1-yl-N-phenylamino)-phenyl]-9H-fluorene,
9,9-Bis[4-(N,N'-bis-naphthalen-2-yl-N,N'-bis-phenyl-amino)-phenyl]-9H-fluorene,
PAPB N,N'-bis(phenanthren-9-yl)-N,N'-bis(phenyl)-benzidine,
2,7-Bis[N,N-bis(9,9-spiro-bifluoren-2-yl)-amino]-9,9-spiro-bifluorene,
2,2'-Bis[N,N-bis(biphenyl-4-yl)amino]9,9-spiro-bifluorene,
2,2'-Bis(N,N-di-phenyl-amino)9,9-spiro-bifluorene,
Di-[4-(N,N-ditolyl-amino)-phenyl]cyclohexane,
2,2',7,7'-tetra(N, N-di-tolyl)amino-spiro-bifluorene,
N,N,N',N'-tetra-naphthalen-2-yl-benzidine,
Spiro-2NPB 2,2',7,7'-tetrakis[N-naphthalenyl(phenyl)-amino]-9,9-spirobifluorene,
Spiro-TTB (2,2',7,7'-Tetrakis-(N,N'-di-p-methylphenylamino)-9,9'-spirobifluorene),
TIOPC titanium oxide phthalocyanine,
CUPC copper phthalocyanine,
F4-TCNQ 2,3,5,6-Tetrafluoro-7,7,8,8-tetracyano-quinodimethane
4,4',4"-Tris(N-3-methylphenyl-N-phenyl-amino)triphenylamine
4,4',4"-Tris(N-(2-naphthyl)-N-phenyl-amino)triphenylamine
4,4',4"-Tris(N-(1-naphthyl)-N-phenyl-amino)triphenylamine
4,4',4"-Tris(N,N-diphenyl-amino)triphenylamine
PPDN Pyrazino[2,3-f][1,10]phenanthroline-2,3-dicarbonitrile
MeO-TPD N,N,N',N'-Tetrakis(4-methoxyphenyl)benzidine
Spiro-MeOTAD $N^2,N^2,N^{2'},N^{2'},N^7,N^7,N^{7'},N^{7'}$-octakis(4-methoxyphenyl)-9,9'-spirobi[9H-fluorene]-2,2',7,7'-tetramine The possible matrix materials for the organic p-doped region of the charge carrier generation layer are, however, not restricted to said materials. Other matrix materials, such as, for example, commercially available NHT5, NHT49, NHT51 of Novaled, HTM014, HTM081, HTM163 from Merck, EL-301 and EL-022t of Hodogaya and similar commercially available materials are likewise suitable. Said hole-conducting matrix materials have proven successful and allow particularly good electrical properties for the p-doped region of the charge carrier generation layer.

According to another preferred embodiment, the matrix materials or matrix-forming materials are materials from the group of triarylamines and/or materials from the group of spiro compounds.

The materials are preferably materials which have both a triarylgroup and a spirocentre.

According to a preferred embodiment of the invention, the degree of doping in % by volume of the zinc complex in relation to the p-doped region is in the range from ≥0.1% to ≤50%. The degree of doping is preferably from ≥0.5% by volume to ≤25% by volume, even more preferably ≥1% by volume to ≤20% by volume, even more preferably ≥3% by volume to ≤15% by volume and most preferably ≥5% by volume to ≤10% by volume. Measurements of the inventors prove that in these regions the best conductivities can be achieved for application in organic electronic components, for example OLEDs. In addition, it has been found that sufficiently high tunnel currents at p-n junctions can also be obtained in these regions.

A further development of the invention relates to the component according to the invention, wherein the charge carrier generation layer additionally has an n-conducting region, preferably an organic n-conducting region. The n-conducting region can preferably be an n-conducting layer, in particular an area-covering, continuous layer.

According to one embodiment, the n-conducting region has a common interface with the organic p-doped region. In this way, a p-n transition is obtained.

According to a different embodiment, an intermediate region can also be formed between the n-conducting region and the p-doped region, for example in the form of an intermediate layer. The charge carrier pair separation takes place in each case at the p-n junction with or without an intermediate region. In both cases, with and without an intermediate region, the p-doped region can be a p-doped layer and at the same time the n-conducting region can be an n-conducting layer, wherein the p-doped layer and the n-conducting layer can have a common interface, or wherein an intermediate region in the form of an intermediate layer is present between the p-doped layer and the n-conducting layer.

An embodiment of the component of the invention has an organic n-doped region as the n-conducting region.

The organic n-doped region preferably has an electron-conducting matrix and an n-type dopant, which is introduced into the electron-conducting matrix. In particular, the n-type dopant can be homogeneously distributed in the electron-conducting matrix. The n-doped region can preferably be produced by co-evaporation of a matrix-forming material and of the n-type dopant. For example, the n-doped region can be an n-doped layer. For example, the n-doped region can consist of the n-type dopant and the electron-conducting matrix.

According to a further preferred embodiment, the organic n-conducting region has a matrix, in particular an electron-conducting matrix. For example, the electron-conducting matrix can be doped with an n-type dopant; however, a sufficiently conductive matrix without an n-type dopant is also conceivable.

The material for the electron-conducting matrix of the n-conducting region and/or of the n-conducting layer can be selected from a group consisting of the commercially available matrix materials NET-18, NET-218 from Novaled, Et093 from Idemitsu Kosan, EM020, EM033, EM034, ETM036 from Merck. In addition, the material for the electron-conducting matrix of the n-conducting region and/or of the n-conducting layer can be selected from the group of the following materials:

2,2',2"-(1,3,5-Benzinetriyl)-tris(1-phenyl-1-H-benzimidazole),
2-(4-Biphenylyl)-5-(4-tert-butylphenyl)-1,3,4-oxadiazole,
2,9-Dimethyl-4,7-diphenyl-1,10-phenanthroline (BCP),
8-Hydroxyquinolinolato-lithium,
4-(Naphthalen-1-yl)-3,5-diphenyl-4H-1,2,4-triazole,
1,3-Bis[2-(2,2'-bipyridine-6-yl)-1,3,4-oxadiazo-5-yl]benzen, 4,7-Diphenyl-1,10-phenanthroline (BPhen),
3-(4-Biphenylyl)-4-phenyl-5-tert-butylphenyl-1,2,4-triazol,
Bis(2-methyl-8-quinolinolate)-4-(phenylphenolato)aluminium, 6,6'-Bis[5-(biphenyl-4-yl)-1,3,4-oxadiazo-2-yl]-2,2'-bipyridyl,
2-phenyl-9,10-di(naphthalen-2-yl)-anthracene,
2,7-Bis[2-(2,2'-bipyridine-6-yl)-1,3,4-oxadiazo-5-yl]-9,9-dimethylfluorene,
1,3-Bis[2-(4-tert-butylphenyl)-1,3,4-oxadiazo-5-yl]benzen,
2-(naphthalen-2-yl)-4,7-diphenyl-1,10-phenanthroline,
2,9-Bis(naphthalen-2-yl)-4,7-diphenyl-1,10-phenanthrolin,
Tris(2,4,6-trimethyl-3-(pyridin-3-yl)phenyl)borane,
1-methyl-2-(4-(naphthalen-2-yl)phenyl)-1H-imidazo[4,5-f][1,10]phenanthroline,
Phenyl-dipyrenyl phosphine oxides, naphthalene tetracarboxylic dianhydride and its imides, perylenetetracarboxylic dianhydride and the imides thereof, materials based on silanols having a silacyclopentadienoic unit. Mixtures of the aforementioned substances are also possible.

According to a preferred embodiment, the n-conducting region and/or the n-conducting layer as a n-dopant have one or more materials selected from a group consisting of NDN-1, NDN-26 of Novaled, Na, Ca, Mg, Ag, Cs, Li, Mg, Yb, $Cs_2CO_3$ and $Cs_3PO_4$.

These materials are characterized by the necessary electrical properties for use in the n-conducting region. Deposition of the electron-conducting matrix and of the n-type dopant is possible by means of evaporation or sublimation by means of gas phase processes. If an n-type dopant is present, which is preferred, the deposition can be effected by means of co-evaporation. However, a deposition can also be carried out by means of liquid processing.

As already mentioned, according to a particularly preferred embodiment, an intermediate region can be present between the organic p-doped region and the n-conducting region. For example, the charge carrier generation layer can have a p-doped layer and an n-conducting layer, between which the intermediate region is arranged as an intermediate layer. The intermediate layer can be, for example, a continuous, area-covering layer.

The intermediate region is arranged both directly at, that is to say in direct mechanical and/or electrical contact with, the n-conducting region and at the p-doped region. The intermediate region thus has a common interface with the p-doped region and a common interface with the n-conducting region. In particular, the n-conducting region and the organic p-doped region are connected to one another via the intermediate region. With the aid of the intermediate region, it is possible to avoid undesirable reactions between the organic p-doped region and the n-conducting region. In this way, a significantly more stable charge carrier generation layer and thus a significantly more stable component can be produced.

Different materials can be used for the configuration of the intermediate region. The intermediate region can comprise or consist of insulating, organic and inorganic materials. Some suitable embodiments are specified below by way of example.

The intermediate region, designed, for example, as an intermediate layer, can have insulating materials, for example aluminum oxide, or be formed therefrom. In this case, the intermediate layer represents a tunnel barrier for the charge carriers. At the same time, the intermediate layer separates the n-conducting region and the p-doped region, which can otherwise react with one another at the interface and can thereby lose their function in the component.

The intermediate region can also have organic materials or be formed from organic materials (that is to say an organic intermediate region or an organic intermediate layer) which have intermediate states which increase the tunneling probability. The charge carriers can then move between the p-doped region and the n-conducting region in addition to "tunneling", through the so-called hopping mechanism, from intermediate state to intermediate state of the material of the organic intermediate layer. As a result, the efficiency of the component can be increased. In this case, the stabilizing effect of the intermediate region can be used and at the same time the efficiency can be improved.

The intermediate region can also comprise or consist of an inorganic material. The inorganic intermediate region, designed, for example, as an inorganic intermediate layer, has a second charge carrier transport mechanism. The second charge carrier transport mechanism transports the charge carriers through "tunnels", it thus represents a tunnel barrier for the charge carriers. The second charge carrier transport mechanism has no hopping mechanism in comparison to the first charge carrier transport mechanism, since the materials of the inorganic intermediate layer do not have any intermediate states which induce a hopping mechanism. The first charge carrier transport mechanism thus differs at least partially from the second charge carrier transport mechanism. In this case, too, the intermediate region has a positive effect on the stability of the component.

According to at least one embodiment, the intermediate region is an organic intermediate region.

According to one embodiment, the organic intermediate region has a material or a combination of materials which is/are selected from the group consisting of phthalocyanine, at least one or exactly one phthalocyanine derivative, naphthalocyanine, at least one or exactly one naphthalocyanine derivative, porphyrin and at least one or exactly one porphyrin derivative.

According to at least one embodiment, the organic intermediate region comprises at least one phthalocyanine and/or a phathalocyanin derivative or consists thereof. The phthalocyanine and/or phthalocyanine derivative is coordinated in each case on a metal or a metal compound. The metal or the metal compound is selected from a group comprising copper (Cu), zinc (Zn), cobalt (Co), aluminium (Al), nickel (Ni), iron (Fe), tin oxide (SnO), manganese (Mn), magnesium (Mg), vanadium oxide (VO) and titanium oxide (TiO).

The materials disclosed in DE 10 201 3 107 113 A1 and/or DE 10 201 0 017 361 A1 and/or DE 10 201 2 204 327 A1 can be used for the organic intermediate region. The disclosure content of the above-mentioned disclosure documents is hereby incorporated by reference.

According to at least one embodiment, the intermediate region is an inorganic intermediate region. The inorganic intermediate region has at least one metal or semi-metal which is selected from a group consisting of lithium (Li), sodium (Na), potassium (K), rubidium (Rb), cesium (Cs), beryllium (Be), magnesium (Mg), calcium (Ca), strontium (Sr), barium (Ba), boron (B), aluminum (Al), silver (Ag), ytterbium (Yb), gallium (Ga), indium (In), thallium (Tl) and combinations thereof.

According to at least one embodiment, the inorganic intermediate region has at least one metal or semi-metal which is selected from a group comprising lithium (Li), sodium (Na), potassium (K), rubidium (Rb), cesium (Cs), beryllium (Be), magnesium (Mg), calcium (Ca), strontium (Sr), barium (Ba), boron (B), aluminium (Al), silver (Ag), ytterbium (Yb), gallium (Ga), indium (In), thallium (Tl) and combinations thereof.

According to at least one embodiment, the inorganic intermediate region has a base metal or consists thereof. In particular, the inorganic intermediate region is designed as an n-type dopant. The inorganic intermediate layer is preferably formed from calcium and/or calcium is set up as an n-type dopant. Calcium increases the band bending at the interface, i.e. it therefore acts as an n-type dopant at the interface n-conducting region and at the same time separates the electron-conducting and hole-conducting organic layers from one another, which means that it has an insulating effect.

According to a particularly preferred embodiment, the intermediate region is designed as an intermediate layer and has a thickness of between 0.5 nm and 10 nm. The inventors have found that sufficiently high tunnel currents are available in this region and a good efficiency of the component can be achieved and at the same time a good separation of the n-conducting and the p-doped region can be achieved, so that the materials of these regions do not undergo any undesirable reactions with one another. Intermediate layers of this thickness therefore allow good efficiency and at the same time a high stability of the charge carrier generation layer and thus of the component containing it. Even more preferably, a thickness of 1 nm to 8 nm is preferred, and most preferred is a thickness of 2 to 6 nm. The balance between efficiency and service life is particularly pronounced in these regions.

According to a further embodiment, the intermediate region can have or consist of two intermediate layers, wherein the first intermediate layer differs from the second intermediate layer in terms of its material. The prerequisite is that the layer thickness of both layers taken together does not exceed 10 nm.

The invention further relates to the organic electronic component comprising
an anode,
a first emitter layer,
a second emitter layer,
a cathode,
wherein the charge carrier generation layer is arranged between the first and second emitter layers.

The component thus has at least two electrodes, an anode and a cathode, by means of which a voltage can be applied to the component. The emitter layers in turn can emit electromagnetic radiation, for instance in the form of visible light or UV light, when an external voltage is applied. The component is then a radiation-emitting component.

According to at least one embodiment, at least one of the electrodes is transparent. Here and hereinafter, "transparent layer" denotes a layer which is transmissive to visible light. In this case, the transparent layer can be clearly translucent or at least partially light-diffusing and/or partially light-absorbing, so that the transparent layer can, for example, also be diffusely or milkily translucent. Particularly preferably, a layer which is referred to here as transparent is as light-transmissive as possible, so that in particular the absorption of light generated in the emitter layers during operation of the organic electronic component is as low as possible.

According to at least one embodiment, both electrodes are transparent. The light generated in the at least two emitter layers can thus be radiated in both directions, i.e. through both electrodes. In the event that the organic electronic component has a substrate, this means that the light passes through the substrate, which is then likewise transparent, and can be radiated into the direction facing away from the substrate. Furthermore, in this case, all layers of the organic electronic component can be transparent, so that the component forms a transparent OLED. In addition, it can also be possible for one of the two electrodes, between which the emitter layers and the charge carrier generation layer are arranged, to be non-transparent and preferably reflective, so that the light generated in the at least two emitter layers can be emitted only in one direction through the transparent electrode. In particular, this direction is the main beam direction or main direction x. Where the electrode arranged on the substrate is transparent and the substrate is also transparent, this is also referred to as a so-called bottom emitter, while in the case where the electrode is arranged facing away from the substrate and is transparent, this is referred to as a so-called top emitter.

According to at least one embodiment, one electrode is transparent and the further electrode is formed in a reflective manner, so that the radiation generated in the emitter layers is coupled out in the main direction x via the transparent electrode. In particular, the electrode formed in a transparent manner is arranged on a substrate, which is then likewise transparent. The component is then formed as a so-called bottom emitter.

A transparent conductive oxide, for example, can be used as the material for a transparent electrode. Transparent conductive oxides, briefly "TCOs", are generally metal oxides, such as, for example, zinc oxide, tin oxide, cadmium oxide, titanium oxide, indium oxide or indium tin oxide (ITO) in addition to binary metal-oxygen compounds, such as, for example, ZnO, $SnO_2$ or $In_2O_3$, ternary metal-oxygen compounds, such as, for example, $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides to the group of TCOs. In this case, the TCOs do not necessarily correspond to a stoichiometric composition and can furthermore be p- or n-doped. In particular, the transparent material is indium tin oxide (ITO).

A preferred embodiment has the following arrangement: the first emitter layer is arranged on the anode, the charge carrier generation layer is arranged on the first emitter layer and the second emitter layer is arranged on the charge carrier generation layer. The cathode is finally arranged on the second emitter layer.

It is also possible, for example, for the component to have a substrate which can, for example, be applied on the outside of the cathode or anode, in particular in direct proximity to the cathode or anode. For example, the anode can be arranged directly on the substrate.

The n-conducting region of the charge carrier generation layer is arranged on the side of the charge carrier generation layer facing the anode, and the p-doped region is arranged on the side of the charge carrier generation layer facing the cathode.

In this case, the term "on" can in each case mean directly, but layers can also be present in between.

The described arrangement represents an electronic component which has two OLED sub-units, which are connected in series by means of the charge carrier generation layer. Higher luminous densities can thus be achieved with the same current. Such devices in particular offer longer lifetimes than conventional organic light-emitting diodes and at the same time a more homogeneous luminance.

According to one embodiment, the cathode comprises aluminum, copper or silver. Suitable electrode materials are, in addition, AgMg alloys.

According to a further embodiment, the anode has a material selected from the group consisting of indium tin oxide (=ITO) and aluminum zinc oxide (abbreviated to AZO). The anode can also consist of a material from said group.

According to another embodiment of the invention, the first and second emitter layers each have, independently of one another, a matrix material and, independently of one another, an emitter material. These can in each case be materials as are currently used in emitter layers. The emitter material can be a metal complex, for example an iridium complex or another conventional radiation-emitting complex.

In a development, both emitter layers are identical. However, it is preferred that the emitter layers emit electromagnetic radiation of different wavelengths, that is to say that the emitter layers are different. Colour mixtures can thus be obtained in the radiation emitted by the component. For example, an emitter layer can also contain two emitter materials, which emit radiation of different wavelengths. White light can thus be generated, for example, together with the second emitter layer.

According to at least one embodiment, the organic electronic component has a substrate. In particular, one of the two electrodes is arranged on the substrate. The substrate can comprise, for example, one or more materials in the form of a layer, a plate, a film or a laminate which are selected from glass, quartz, plastic, metal, silicon, wafer. In particular, the substrate has glass or consists thereof.

According to a preferred embodiment, the component according to the invention additionally comprises a hole injection layer between the anode and the first emitter layer and/or an electron injection layer between the second emitter layer and the cathode. The use of hole-injection and/or electron-injection layers improves the performance of radiation-emitting components.

Further layers, for example electron- and/or hole-blocking layers, are also possible. The use of such layers has proven successful in organic electronic components.

The material for a hole injection layer can be selected from a group consisting of:
HAT-CN, F16CuPc, LG-101, a-NPD,
NPB (N,N'-Bis(naphthalen-1-yl)-N,N'-bis(phenyl)-benzidine), beta-NPB N,N'-Bis(naphthalen-2-yl)-N,N'-bis(phenyl)-benzidine),
TPD (N,N'-Bis(3-methylphenyl)-N,N'-bis(phenyl)-benzidine), Spiro TPD (N,N'-Bis(3-methylphenyl)-N,N'-bis(phenyl)-benzidine),
Spiro-NPB (N,N'-Bis(naphthalen-1-yl)-N,N'-bis(phenyl)-spiro), DMFL-TPD N,N'-Bis(3-methylphenyl)-N,N'-bis(phenyl)-9,9-dimethyl-fluorene),
DMFL-NPB (N,N'-Bis(naphthalen-1-yl)-N,N'-bis(phenyl)-9,9-dimethyl-fluorene),
DPFL-TPD (N,N'-Bis(3-methylphenyl)-N,N'-bis(phenyl)-9,9-diphenyl-fluorene),
DPFL-NPB (N,N'-Bis(naphthalen-1-yl)-N,N'-bis(phenyl)-9,9-diphenyl-fluorene),
Spiro-TAD (2,2',7,7'-Tetrakis(N,N-diphenylamino)-9,9'-spirobifluorene),
9,9-Bis[4-(N,N-bis-biphenyl-4-yl-amino)phenyl]-9H-fluorene, 9,9-Bis[4-(N,N-bis-naphthalen-2-yl-amino)phenyl]-9H-fluorene, 9,9-Bis[4-(N,N'-bis-naphthalen-2-yl-N,N'-bis-phenyl-amino)-phenyl]-9H-fluorine,
N,N'-bis(phenanthren-9-yl)-N,N'-bis(phenyl)-benzidine,
2,7-Bis[N,N-bis(9,9-spiro-bifluorene-2-yl)-amino]-9,9-spiro-bifluorene,
2,2'-Bis[N,N-bis(biphenyl-4-yl)amino]9,9-spiro-bifluoren, 2,2'-Bis(N,N-di-phenyl-amino)9,9-spiro-bifluoren, Di[4-(N,N-ditolyl-amino)-phenyl]cyclohexane,
2,2',7,7'-tetra(N, N-di-tolyl)amino-spiro-bifluorene, N,N,N',N'-tetra-naphthalen-2-yl-benzidine, HTM081, HTM163, HTM222, NHT49, NHT51 and mixtures of these compounds.

One or more materials can be used as the p-type dopant for the hole-injection layer, which are selected from a group consisting of $MoO_x$, $WO_x$, $VO_x$, Cu(I)pFBz (pFBz: Pentafluorobenzoate), Bi(III)pFBz, F4-TCNQ (2,3,5,6-Tetrafluoro-7,7,8,8-tetracyanoquinodimethane), NDP-2 and NDP-9. The terms HTM081, HTM163, HTM222, NHT49, NHT51, NET-18, NET-218, ET093, ETM020, ETM033, ETM034, ETM036, NDN-1 and NDN-26 are manufacturers' names for products by Merck, Novaled and/or Idemitsu.

The material for an electron injection layer can be selected from a group consisting of:
NET-18, NET-218, ET093, ETM020, ETM033, ETM034, ETM036, 2,2',2"-(1,3,5-Benzinetriyl)-tris(1-phenyl-1-H-benzimidazole),
2-(4-Biphenylyl)-5-(4-tert-butylphenyl)-1,3,4-oxadiazole, 2,9-Dimethyl-4,7-diphenyl-1,10-phenanthroline (BCP),
8-Hydroxyquinolinolato-lithium,
4-(Naphthalen-1-yl)-3,5-diphenyl-4H-1,2,4-triazole,
1,3-Bis[2-(2,2'-bipyridine-6-yl)-1,3,4-oxadiazo-5-yl]benzen, 4,7-Diphenyl-1,10-phenanthroline (BPhen),
3-(4-Biphenylyl)-4-phenyl-5-tert-butylphenyl-1,2,4-triazol, Bis(2-methyl-8-quinolinolate)-4-(phenylphenolato)aluminium, 6,6'-Bis[5-(biphenyl-4-yl)-1,3,4-oxadiazo-2-yl]-2,2'-bipyridyl, 2-phenyl-9,10-di(naphthalen-2-yl)-anthracene,
2,7-Bis[2-(2,2'-bipyridine-6-yl)-1,3,4-oxadiazo-5-yl]-9,9-dimethylfluorene,
1,3-Bis[2-(4-tert-butylphenyl)-1,3,4-oxadiazo-5-yl]benzene, 2-(naphthalen-2-yl)-4,7-diphenyl-1,10-phenanthroline,
2,9-Bis(naphthalen-2-yl)-4,7-diphenyl-1,10-phenanthroline, Tris(2,4,6-trimethyl-3-(pyridin-3-yl)phenyl)borane,
1-methyl-2-(4-(naphthalen-2-yl)phenyl)-1H-imidazo[4,5-f][1,10]phenanthroline,
Phenyl-dipyrenyl phosphine oxides, naphthalene tetracarboxylic dianhydride and its imides, perylenetetracarboxylic dianhydride and the imides thereof, materials based on silanols having a silacyclopentadienoic acid unit and mixtures of the aforementioned substances. The n-type dopant used may be one or more materials selected from a group consisting of NDN-1, NDN-26, Na, Ca, Mg, Ag, Cs, Li, Mg, Yb, $Cs_2CO_3$ and $Cs_3PO_4$.

According to one embodiment of the above-described embodiments of the component, the component has at least one further charge carrier generation layer and at least one further emitter layer. An arrangement of this type has a total of at least three emitter layers and at least two charge carrier generation layers. For example, the emitter layers can emit radiation of a different spectral range and thus allow colour mixtures. In particular, a white light-emitting component can thus be made possible. However, it is also conceivable that two or even three of the emitter layers are identical, thus enabling emission of particularly high luminance in a specific wavelength range.

The present invention also relates to the use of a zinc complex containing at least one ligand L of the following structure:

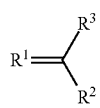

wherein $R^1$ and $R^2$ can be; independently of one another; oxygen, sulfur, selenium, NH or $NR^4$, wherein $R^4$ is selected from the group consisting of alkyl or aryl and can be connected to $R^3$; and $R^3$ is selected from the group consisting of alkyl, long-chain alkyl, cycloalkyl, haloalkyl, at least partially halogenated long-chain alkyl, halocycloalkyl, aryl, arylenes, haloaryl, heteroaryl, heteroarylenes, heterocycloalkylenes, heterocycloalkyl, halogen-heteroaryl, alkenyl, haloalkenyl, alkinyl, haloalkinyl, ketoaryl, haloketoaryl, ketoheteroaryl, ketoalkyl, haloketoalkyl, ketoalkenyl, haloketoalkenyl, haloalkylaryl, haloalkyl heteroaryl, wherein, in the case of suitable residues, one or more non-adjacent $CH_2$ groups can be replaced independently of one another by —O—, —S—, —NH—, —NR°°°—, —SiR°R°°—, —CO—, —COO—, —COR°OR°°—, —OCO—, —OCO—O—, —$SO_2$—, —S—CO—, —CO—S—, —O—CS—, —CS—O—, —CY1=CY2 or —C≡C— in such a way that O and/or S atoms are not directly connected to one another, likewise optionally substituted with aryl or heteroaryl, preferably containing 1 to 30 C atoms (terminal $CH_3$ groups are understood as $CH_2$ groups in the sense of $CH_2$—H), as the p-type dopant in charge carrier generation layers.

All properties described in connection with the organic electronic component for the zinc complex relate equally to the zinc complex mentioned here.

According to a preferred embodiment, the use of the zinc complex relates to the use in the p-doped region of a charge carrier generation layer, in particular in a p-doped layer at a p-n junction.

Further details, features and advantages of the subject matter of the invention will become apparent from the sub-claims and from the following description of the figures and the associated general production methods and specific examples.

In the figures:

FIG. 1 schematically illustrates the principle of charge carrier generation in a charge carrier generation layer.

FIG. 7A shows the current density plotted against the voltage for zinc trifluoroacetate as a p-dopant introduced into a matrix (NHT49, Novaled).

FIG. 7B shows the current density plotted against the voltage for zinc trifluoroacetate as a p-type dopant introduced into a matrix (HTM081 from Merck).

Figure 1:
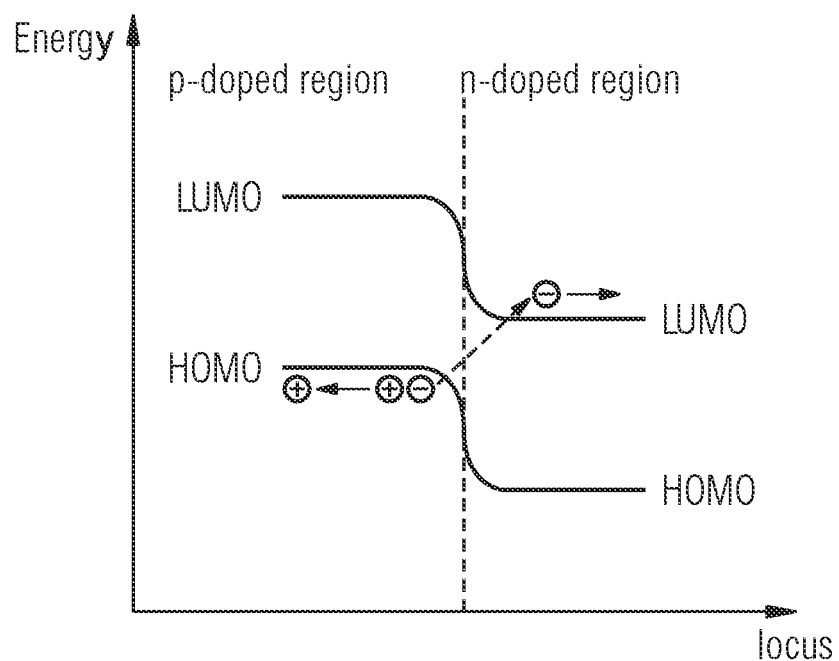

The invention will be explained in more detail below with reference to the figures, in which:

FIG. 1 shows a schematic representation of the principle of charge carrier generation in a charge carrier generation layer. The diagram shows the energy levels as a function of the location within a charge carrier generation layer. In the p-doped organic region of the charge carrier generation layer, the LUMO ("lowest unoccupied molecular orbital", that is to say the unoccupied molecular orbital which is at the lowest point in terms of energy) and the HOMO ("highest occupied molecular orbital", that is to say the occupied molecular orbital which is highest in terms of energy) have in each case particularly high energy levels. In comparison thereto, the energy levels of LUMO and HOMO within the n-conducting region of the charge carrier generation layer are significantly reduced. The HOMO of the p-doped region and the LUMO of the n-conducting region are relatively close in terms of energy. For this reason, under certain circumstances, for example when applying an external voltage, tunneling of an electron from the HOMO of the p-doped region into the LUMO of the n-conducting region of the charge carrier generation layer is possible. The selection of the p-type dopant plays a central role in the position of the energy levels described and thus forms a central prerequisite for the occurrence of a tunnel current in the charge carrier generation layer. The described tunneling of an electron from the HOMO of the p-doped organic region into the LUMO of the n-conducting region results in the generation and separation of a charge carrier pair in the form of a positive charge remaining in the HOMO of the p-doped region and of an electron, i.e. a negative charge, in the LUMO of the n-conducting region. The positive charge within the p-doped organic region can be transported under the influence of an external electric field through the p-doped region of the charge carrier generation layer, while in an analogous manner the negative charge, that is to say the electron, can be transported through the n-conducting region of the charge carrier generation layer. It is also possible that between the p-doped region and the n-conducting region, a thin intermediate layer (having a thickness of a few nanometers) is located. As a result, an additional barrier is created, which also has to be "passed through".

Figure 2:
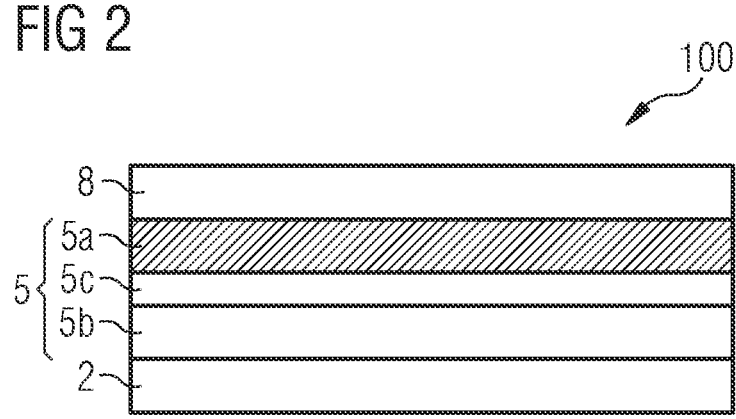
FIG. 2 shows a schematic representation of an organic electronic component according to the invention.

FIG. 2 shows a schematic representation of the layer arrangement in an organic electronic component 100 according to the invention, comprising at least one charge carrier generation layer 5, wherein the charge carrier generation layer comprises at least one organic p-doped region 5a, which contains the zinc complex according to the invention as a p-type dopant. For example, the organic p-doped region 5a can comprise an organic hole-conducting matrix, which contains an organic hole-conducting matrix material into which the zinc complex can be introduced as a p-type dopant. For example, the charge carrier generation layer can furthermore have an n-conducting region 5b, for example in the form of an organic n-doped region, which can have a common interface with the organic p-doped region. However, it is preferred if an intermediate region 5c is present between the n-conducting region 5b and the p-doped region 5a. The intermediate region is preferably configured as an intermediate layer. The n-conducting region 5b and the p-doped region 5a are also preferably designed as layers. The component can furthermore comprise at least one anode 2 and one cathode 8, wherein the charge carrier generation layer 5 is arranged between the anode 2 and the cathode 8.

Figure 3:
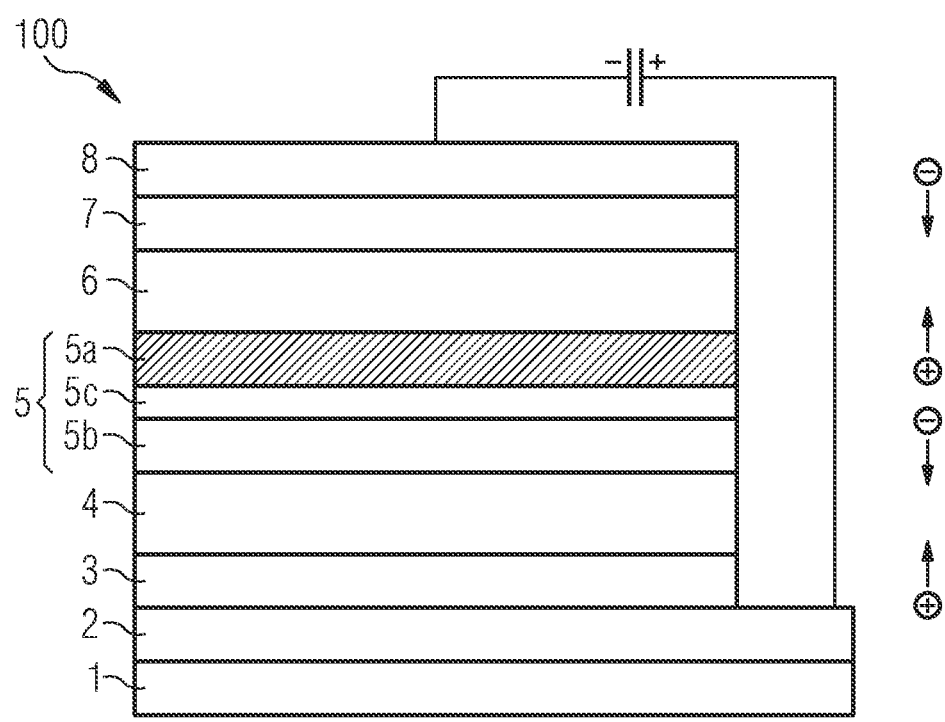
FIG. 3 shows a schematic illustration of a preferred embodiment of an organic electronic component according to the invention.

FIG. 3 shows a schematic illustration of a particularly preferred embodiment of an organic electronic component according to the invention. The component can have a substrate 1, which can be, for example, glass. The anode 2 can be arranged on the substrate, which, for example, can comprise indium tin oxide (ITO). A hole injection layer 3 can be arranged on the anode, and on said hole injection layer a first emitter layer can in turn be arranged. The charge carrier generation layer 5, comprising the p-doped organic region 5a and the n-conducting region 5b, is arranged on the first emitter layer. The p-doped region 5a can have a common interface with the n-conducting region 5b. However, it is preferred if an intermediate layer 5c is present between the two regions, wherein said intermediate layer 5c is connected to both regions 5a and 5b over the entire surface. This serves to avoid undesirable reactions between materials of the regions 5a and 5b and thus ensures an improved stability of the charge carrier generation layer 5. Finally, the second emitter layer 6 is arranged on the charge carrier generation layer, on which an electron injection layer can follow. Finally, the cathode 8 is arranged thereon. An organic electronic component of this type thus comprises at least two emitter layers, between which a charge carrier generation layer is arranged. A component of this type can be seen as a component composed of a plurality of OLEDs, wherein the lower layers form a first OLED up to the charge carrier generation layer and the layers above the charge carrier generation layer form a second OLED. The first OLED connected to the anode is supplied with positive charge carriers by the anode, while it is supplied with electrons, that is to say negative charge carriers, by the charge carrier generation layer 5. In the same way, the second OLED subunit is supplied with electrons via the charge carrier generation layer by the cathode 8, while it draws the required positive charge carriers from the charge carrier generation layer 5. Organic electronic components of this type offer the advantage that two excitons, and not only one exciton, can be generated per injected positive or negative charge carrier into the component. The same current intensity thus leads to a higher light yield, but at the expense of a higher voltage to be applied. The voltage is increased on account of the voltage drop along the OLEDs connected in series.

Figure 4:
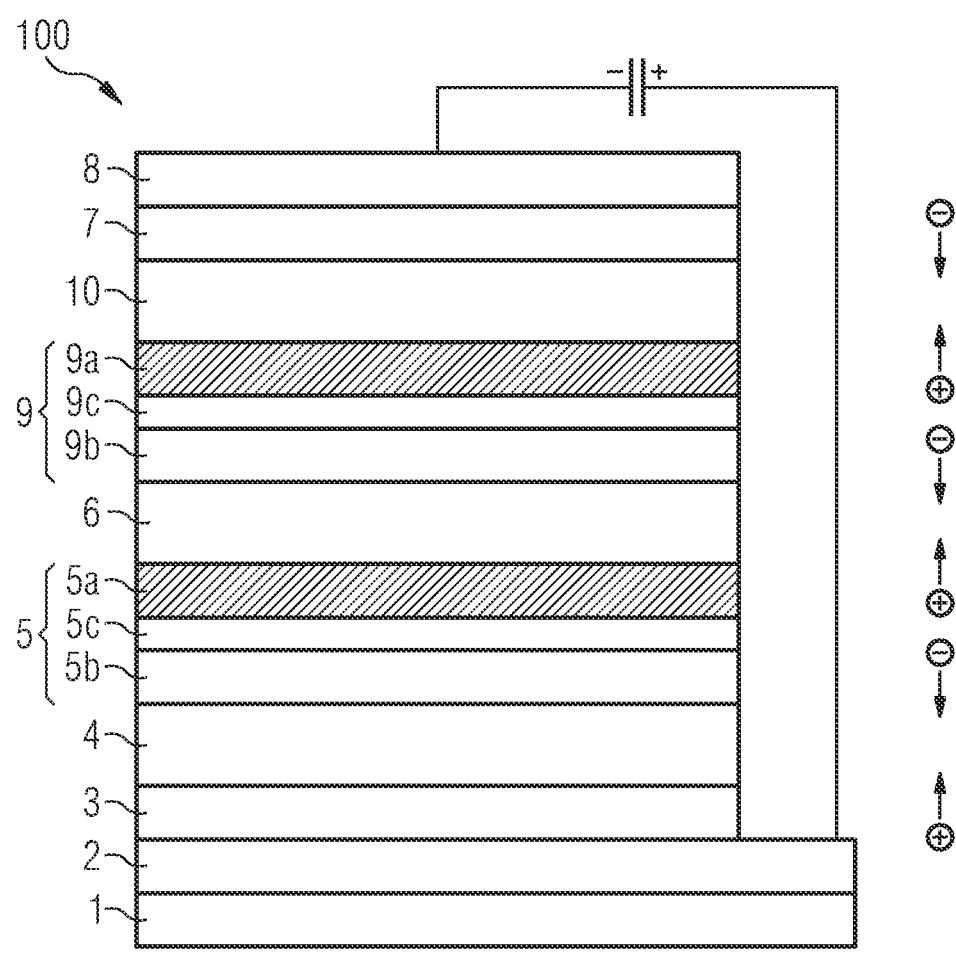
FIG. 4 shows a schematic illustration of a further embodiment of an organic electronic component according to the invention.

FIG. 4 schematically shows a further preferred embodiment of an organic electronic component 100 according to the invention. As is shown in FIG. 4, the component of FIG. 3 is similar in all its essential properties, but also has a second charge carrier generation layer 9, which in turn has an organic p-doped region 9a and an n-conducting region 9b. In addition, it can again have an intermediate region 9c. The regions 9a, 9b and 9c are preferably again designed as layers. For them, the possible materials and other embodiments are preferably based on the same selection as for the regions 5a, 5b and 5c. In addition, the component in FIG. 4 has a third emitter layer 10. The charge carrier generation layer 9 is arranged downstream of the second emitter layer, the third emitter layer 10, which in turn follows the electron injection layer 7, is located on the second emitter layer.

Such a component having at least three emitter layers has the advantage that particularly high color intensities can be achieved with the same current intensity. In this case, it is possible, for example, for all three emitter layers to emit electromagnetic radiation of the same wavelength. In this case, particularly high luminous densities can be produced at this wavelength. However, it is preferred that the three emitter layers emit electromagnetic radiation of different spectral ranges, i.e. different wavelengths. In this way, color mixtures can be formed by the superposition of the light of the different wavelength ranges. In particular, it is possible in this way to generate white light according to a preferred embodiment.

Organic electronic components, as are illustrated in FIGS. 3 and 4, are often also referred to as so-called tandem OLEDs. In comparison to conventional OLEDs, organic electronic components based on this construction principle are distinguished by a significantly higher luminance with the same current. This leads to significantly longer lifetimes and at the same time to improved homogeneity of the luminous surface.

Figure 5A:
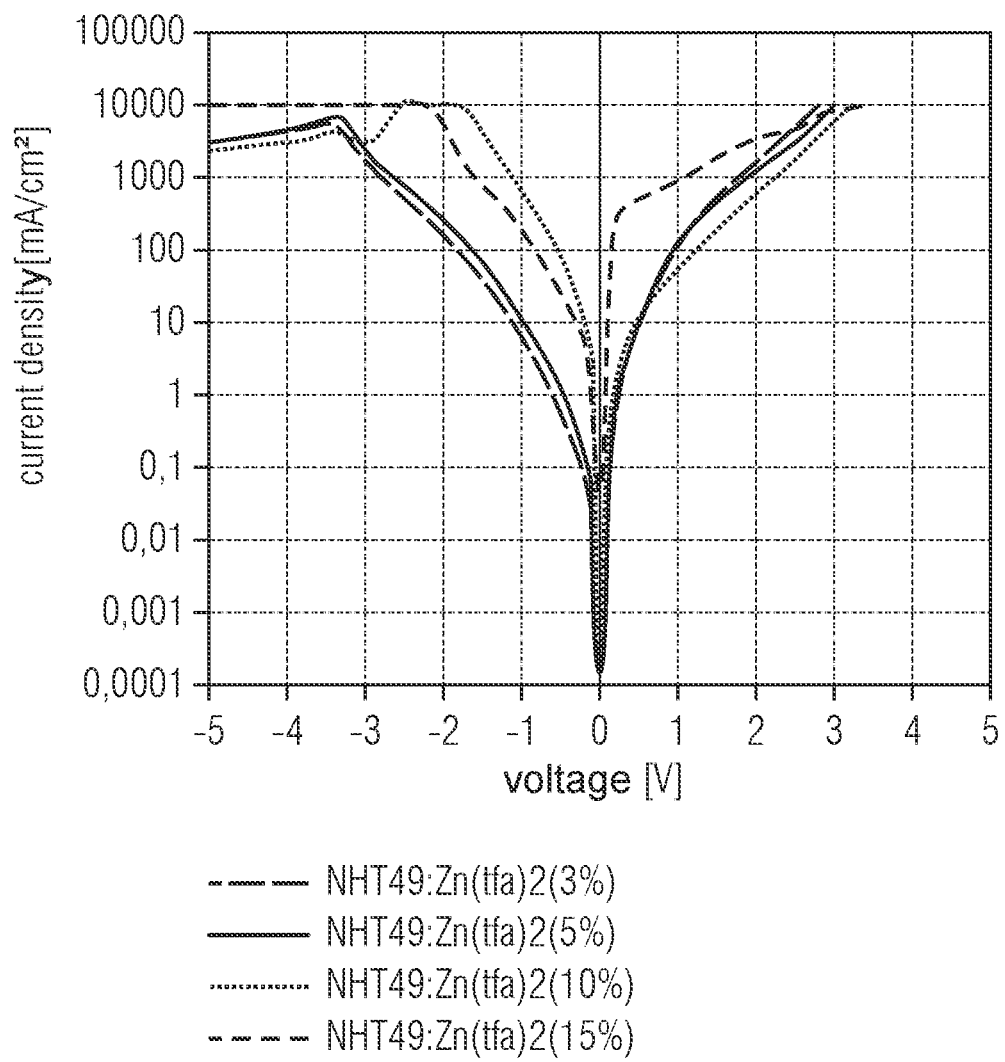
FIG. 5A shows conductivity data for zinc trifluoroacetate as a p-type dopant introduced into a matrix (NHT49 of Novaled).
Figure 5B:
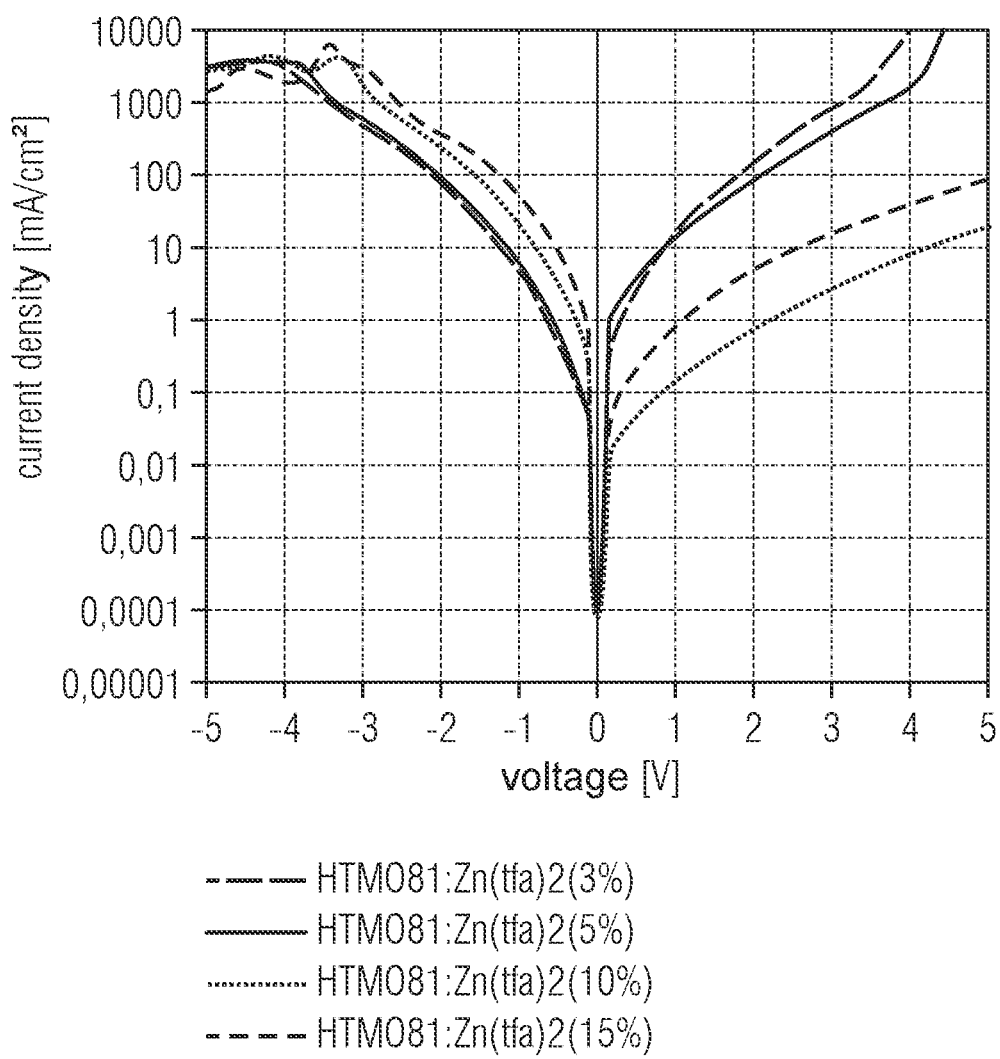
FIG. 5B shows conductivity data for zinc trifluoroacetate as a p-type dopant introduced into a matrix (HTM081 from Merck).

FIGS. 5A and 5B show conductivity measurements on hole-conducting matrix materials doped with zinc complexes according to the invention.

A first important prerequisite for the suitability of a dopant for use in a p-doped organic region is within a charge carrier generation layer, that the dopant has a sufficient p-doping material thickness and enables good hole conduction capabilities in the doped region. It is only in this way that the positive charges generated in the charge carrier generation layer can be efficiently diverted and injected into the adjoining region. The p-type dopant intensities of the zinc complexes according to the invention were therefore examined. The conductivity measurements were carried out on an arrangement having the following structure: An anode made of indium tin oxide (ITO) was loaded with the p-doped matrix material to be measured with a layer thickness of 100 nm. The application was carried out by co-evaporation of the respective matrix material used and of the p-type dopant. A 200 nm thick aluminium layer, which is used as the cathode, is arranged on the p-doped region to be examined.

FIG. 5A shows conductivity data for zinc complexes according to the invention for the example of the zinc trifluoroacetate complex (abbreviated to: $Zn(tfa)_2$) introduced into a hole-conductor matrix, as is usually commercially available. For the measurements in FIG. 5A, the hole waveguide matrix of the type NHT49 from the company Novaled was used for this purpose. The measurements of FIG. 5B show measurements with zinc trifluoro acetate, introduced into another commercially available perforated-conductor matrix material, which is HV081 from Merck. The dopant intensities were examined in both cases as a function of the concentration of the zinc-trifluoro-acetate complex. Measurements between 3 and 15% by volume in each case relative to the p-doped region are illustrated in the graphs. The measurements of the current density against the voltage prove an outstanding p-type dopant strength of the zinc complexes according to the invention for different types of hole-conductor matrix materials as shown in both in FIGS. 5A and 5B. In principle, the zinc complexes according to the invention are suitable in a broad range of different concentrations on the doped layer. Particularly good values are achieved for between 1 and 25% by volume of the zinc complex, wherein further preferred is the range from 3 to 15% by volume. The best values are achieved in each case for between 5 and 10% by volume of the zinc complex in relation to the p-doped organic region and the p-doped organic layer, respectively.

The outstanding conductivity properties, which are demonstrated in FIGS. 5A and 5B, form a necessary, but not a sufficient prerequisite for the suitability of the zinc complexes according to the invention in charge carrier generation layers of organic electronic components according to the invention.

In addition to conductivity, the second property must be that the complexes have to be suitable for producing a tunnelling current at the p-n junction of a charge carrier generation layer.

Figure 6A:
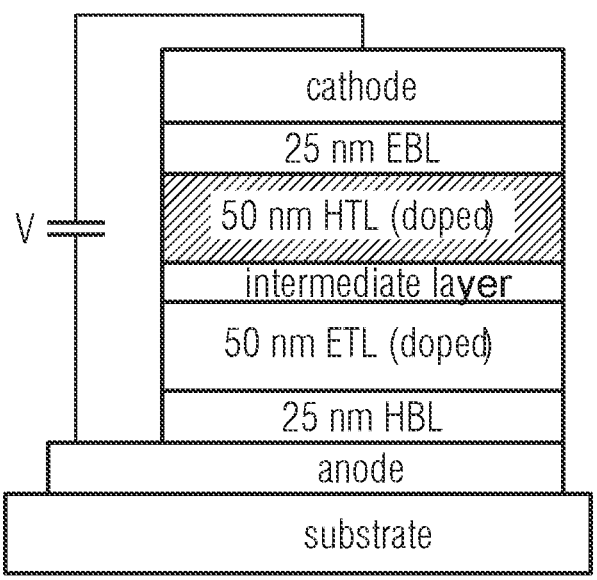
FIG. 6A shows a schematic illustration of a measuring arrangement for determining the suitability for the use of p-type dopants for charge carrier generation layers.

FIG. 6A shows a test arrangement with which precisely this question can be examined. The test arrangement of FIG. 6A simulates the polarity of a tandem OLED. It requires a p-type dopant and allows to determine whether a p-type dopant is suitable for use in a charge carrier generation layer. The test arrangement has a glass substrate followed by an indium tin oxide anode, which is followed by a hole-blocking layer (HBL) with a thickness of 25 nm. This is followed by an electron-transporting layer (=ETL) having a 50 nm thickness and an n-doping. This is followed by the intermediate layer and finally the hole-transporting layer to be tested (=HTL). In the present case, the intermediate layer is a 4 nm thick phthalocyanine derivative layer. The hole transport layer having a thickness of 50 nm is doped with the p-type dopant to be tested. The layer can be obtained, for example, by co-evaporation of the hole-conducting matrix material with the p-type dopant. An electron-blocking layer (=EBL) adjoins this layer having a thickness of 25 nm. The completion forms the cathode layer. The described arrangement makes it possible to test p-type dopants in order to determine whether they allow good tunnel currents.

Figure 6B:
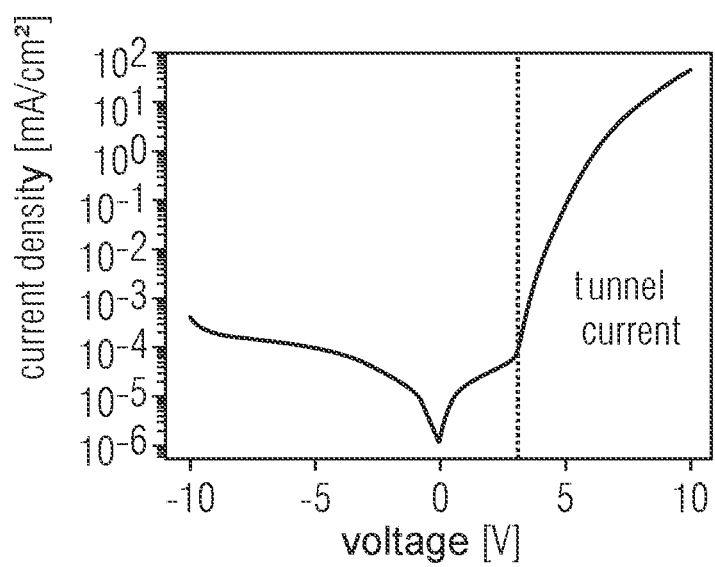
FIG. 6B shows a curve profile for the current density plotted against the voltage, as is desired for a p-type dopant being suitable for charge carrier generation layers.

FIG. 6B shows a theoretical ideal curve profile for a p-doped region of a charge carrier generation layer. The curve profile shows a significant increase in the current density for high positive voltages, which can be attributed to the so-called tunnel effect. Conventional p-type dopants, which are not suitable for charge carrier generation layers, show no or only extremely small tunnel currents. In their case, a corresponding current voltage curve does not look like that in FIG. 6A: The high positive current densities at positive potentials are not given; instead, the graph, viewed about an axis, is symmetrical at 0 V.

In the case of the occurrence of high tunnel currents, the so-called "CGL effect" (CGL=charge generation layer effect) occurs. The occurrence of the tunnel current, that is to say of the CGL effect, thus represents a decisive criterion for the suitability of a p-doping agent for charge carrier migration layers. In contrast to most conventional p-type dopants, the zinc complexes according to the invention surprisingly exhibit a distinct CGL effect, even in the presence of an intermediate layer.

FIGS. 7A and 7B show measurements on zinc complexes according to the invention. The measurements were carried out in each case in the measurement arrangement described in FIG. 6A, wherein the zinc complexes have been introduced into the HTL layer as a p-type dopant. NHT49 of Novaled and HTM081 of Merck served as hole-conductor matrix materials. Results for zinc trifluoroacetate are represented in each case, the concentration of which is specified in volume percent. Measurements are represented for 5, 10 and 15% by volume relative to the p-doped layer. The measurements both in FIGS. 7A and 7B clearly demonstrate the occurrence of high tunnel currents for the zinc complexes according to the invention in a wide contrast region. In this case, a strong CGL effect could already be clearly demonstrated without the final optimization of the dopant content.

The zinc complex described is the first p-type dopant based on a lewis-acidic metal complex which enables the CGL effect, that is to say the required tunneling currents, while at the same time all further requirements such as processability, stability and sufficiently low absorption of the doped layers are satisfied. In particular, it is the first zinc complex of this type. This is thus a p-type dopant of a new substance class for charge carrier generation layers.

Figure 8:
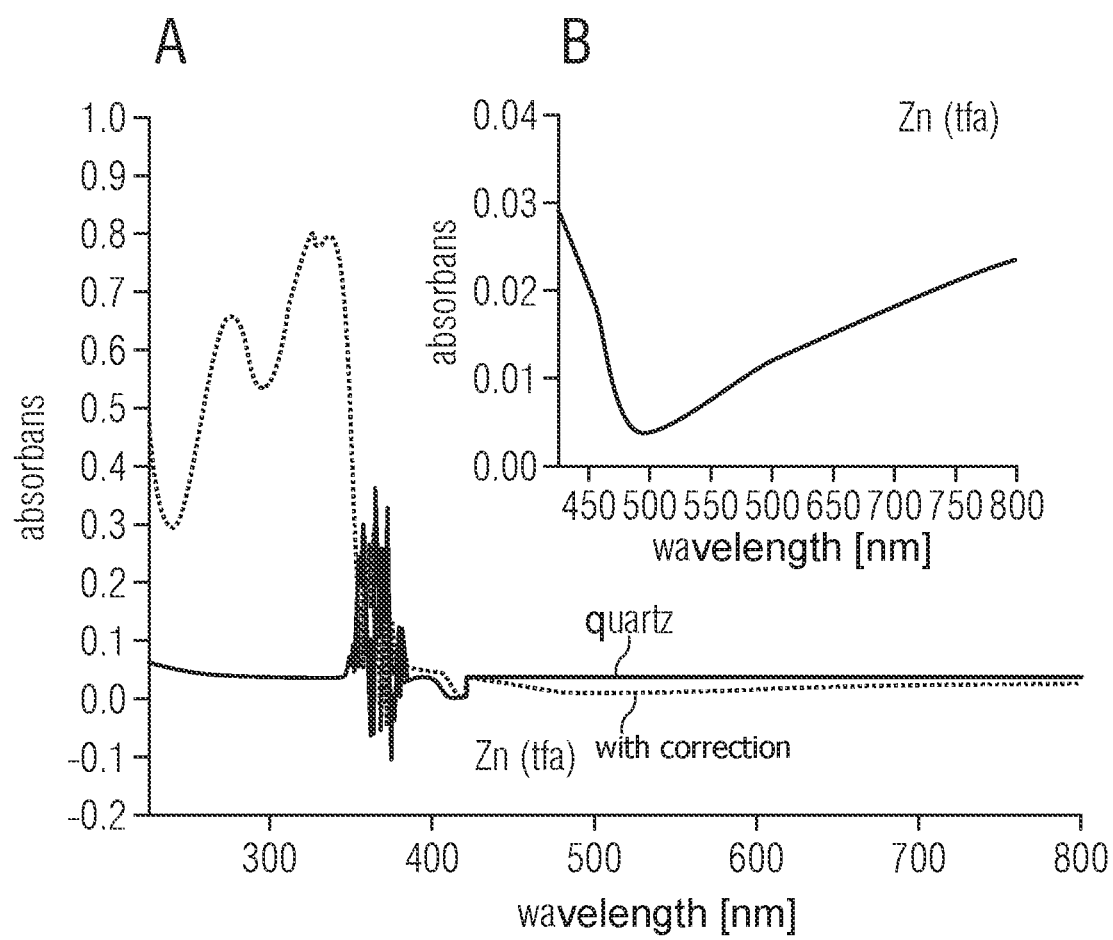
FIG. 8 shows the absorption behaviour of zinc complexes according to the invention using the example of zinc trifluoro acetate.

FIG. 8 shows the absorption spectrum of zinc complexes according to the invention. The absorption measurements were carried out on a Perkin Elmer Lambda 35 UV/VIS spectrometer. A pure quartz substrate was used as a reference in the 2-beam photometer, while a 200 nm thick layer consisting of 5% by volume of zinc trifluoroacetate in HV014 on a quartz substrate served as the sample. FIG. 8A compares the absorption spectra of quartz, which shows an excellent light tolerance, with the absorption behaviour of the complexes according to the invention using the example of zinc trifluoro-acetate (5% by volume coevaporated in HV014, 200 nm layer thickness).

FIG. 8B shows the section between 450 and 800 nm. It can be seen here that the absorbance of the complexes according to the invention is even smaller than 0.03 in the visible region, over wide ranges even smaller than 0.02. Such a low absorbance, which forms a measure of the absorption, is achieved only for a few materials and is shown, the complexes according to the invention are outstandingly suitable for optoelectronic devices, such as, for example, organic light-emitting diodes. In particular, charge carrier generation layers for tandem OLEDs require materials with low absorption. This is the case with devices of this type in which a plurality of OLEDs are stacked one on top of the other, where it is particularly important to reduce losses with regard to luminance and luminous efficiency.

In summary, it can be stated that the zinc complexes according to the invention have high p-type dopant intensities in hole conductor matrix materials and thus have excellent hole transport properties. At the same time, they allow high tunneling currents to be obtained at p-n junctions in charge carrier generation layers, that is to say a strong CGL effect. Furthermore, they are distinguished by low absorption and thus at the same time excellent optical properties for use in organic electronic components, even in the field of optoelectronics.

In the following, possible production paths for the zinc complexes according to the invention will be described briefly.

The zinc complexes can be obtained, for example, by reacting di-alkyl- or di-aryl-zinc with the corresponding carboxylic acids or derivatives thereof. The substitution of the alkyl or aryl ligands of the starting complexes of the zinc proceeds in several steps, wherein the substitution can also be incomplete. Preferably, the substitution is carried out completely. This is represented below by way of example for a two-stage reaction, which can also be stopped after the first stage, for example:

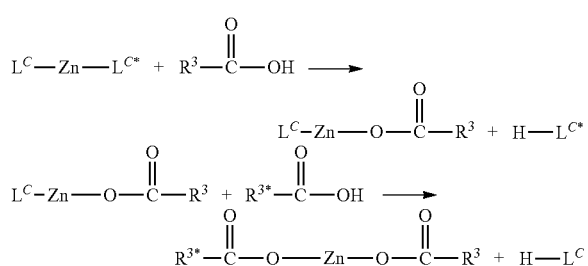

Explanation Relating to the Designations:

$L^C$ here corresponds to the previously described ligand $L^C$ and is an alkyl or aryl. $L^{C*}$ is likewise an alkyl or aryl, independently of $L^C$, wherein $L^C$ and $L^{C*}$ can be identical or different. For the indicated exemplary production method, $R^3$ corresponds to the radical $R^3$ of the ligand L of the zinc complex according to the invention. The carboxylate comprising $R^3$ consequently corresponds in this example to the ligand L of the finished zinc complex (i.e. $L=R^3COO^-$).

It is also possible to obtain the mixed aryl/alkyl carboxylates by means of comproportionation:

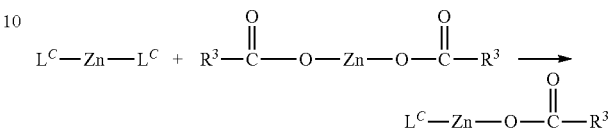

If the substituents $L^C$ are also fluorinated, a class of mixed alkyl/aryl-zinc dopants is obtained. In this way, the doping strength, volatility and solubility can be adjusted not only by the carboxylate ligand $R^3COO^-$ but also by the ligand $L^C$ largely independently of the sublimation temperature.

In the same way as via the synthesis which is formally illustrated here, oligomeric structures or clusters are also accessible.

The synthesis of some zinc complexes will be described below by way of example.

EXAMPLE I

Example I relates to a zinc pentafluorobenzoate complex, $Zn(pfb)_2$, which has been obtained on the synthesis route described below. The formula $Zn(pfb)_2$ is a stoichiometric formula. It is not to be regarded as limiting with regard to the coordination and the structure of the zinc complex, but merely specifies the stoichiometric ratios.

30.59 mmol of pentafluorobenzoic acid are dissolved in 80 ml of toluene and cooled to 0° C. 15.29 mmol of diethylzinc solution (15% in toluene) is diluted with 20 ml of toluene, likewise cooled and carefully added drop by drop to the pentafluorobenzoic acid solution under protective gas. The solution is brought to room temperature with stirring. After about one hour, a slightly white precipitate already precipitates out. The mixture is then stirred at a bath temperature of 50° C. for 15 hours. A dense white precipitate is obtained. The solvent is concentrated to a third, the white product is filtered off with suction via a P4 frit and washed three times with cyclohexane and dried under reduced pressure. The yield is: 6.11 g (82%); sublimation range: 215-230° C./10$^{-5}$ mbar.

EXAMPLE II

Example II relates to the production of a zinc complex with 3,5-bis (trifluoromethyl) benzoate ligands, $Zn(3,5\text{-tfmb})_2$. The formula $Zn(3,5\text{-tfmb})_2$ is a stoichiometric formula. It is not to be regarded as limiting with regard to the coordination and the structure of the zinc complex, but merely specifies the stoichiometric ratios.

30.59 mmol of 3,5-(trifluoromethyl) benzoic acid is dissolved in a mixture of 50 ml of toluene and 30 ml of benzene and cooled to 0° c. 15.29 mmol of diethylzinc solution (15% of toluene) diluted with 10 ml of toluene are added drop by drop to this under protective gas, which was likewise cooled. The result is a jelly-like mass, which is stirred at a bath temperature of 90° C. for 18 hours. A slightly turbid solution is then present. The solvent is completely removed in a vacuum, and a white powder remains. Yield: 8.39 g (86%); sublimation range: 260-280° C./10$^{-5}$ mbar.

EXAMPLE III

Example III relates to the production of a zinc complex with trifluoroacetate ligands, abbreviated to Zn(tfa)$_2$. The formula Zn(tfa)$_2$ is a stoichiometric formula. It is not to be regarded as limiting with regard to the coordination and the structure of the zinc complex, but only the stoichiometric ratios exist.

48.16 mmol of trifluoroacetic acid are mixed with 60 mmol of benzene and cooled to 10° C. 22.9 mmol of diethylzinc solution (15% in toluene) are carefully added dropwise thereto, which was diluted with 60 ml of benzene. The mixture is stirred at room temperature for 15 hours and a white precipitate is obtained. One third of the solvent is taken off, the white product is filtered off with suction via a P4 frit and washed three times with cyclohexane. The yield is: 5.55 g (83%); sublimation range 163-173° C./10$^{-5}$ mbar.

The invention is not restricted by the description on the basis of the exemplary embodiments. Rather, the invention encompasses any new feature and also any combination of features, which includes in particular any combination of features in the patent claims, even if this feature or this combination itself is not explicitly specified in the patent claims or exemplary embodiments.

LIST OF REFERENCE NUMERALS 100 organic electronic component
1 substrate
2 anode
3 hole injection layer
4 first emitter layer
5 charge carrier generation layer
5a organic p-doped region
5b n-conducting region
5c intermediate region
6 second emitter layer
7 electron injection layer
8 cathode
9 further charge carrier generation layer
9a organic p-doped region
9b n-conducting region
9c intermediate region
10 third/further emitter layer
Nm nanometer
Vol.-% volume percent
HBL hole-blocking layer
ETL electron-transporting layer
HTL hole transporting layer
EBL electron-blocking layer
G gram
mmol millimole
mbar millibar
V volt
mA milliampere
cm centimeters

The invention claimed is:

1. An organic electronic component having
at least one charge carrier generation layer which has an organic p-doped region containing a zinc complex as the p-dopant, wherein the zinc complex comprises a zinc atom and at least one ligand L of the following structure:

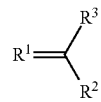

wherein R$^1$ and R$^2$ are, independently of one another, oxygen wherein R$^1$ and/or R$^2$ are coordinated to the zinc atom, and R$^3$ is selected from the group consisting of alkyl, long-chain alkyl, cycloalkyl, haloalkyl, at least partially halogenated long-chain alkyl, halocycloalkyl, aryl, arylenes, haloaryl, heteroaryl, heteroarylenes, heterocycloalkylenes, heterocycloalkyl, halogen-heteroaryl, alkenyl, haloalkenyl, alkinyl, haloalkinyl, ketoaryl, haloketoaryl, ketoheteroaryl, ketoalkyl, haloketoalkyl, ketoalkenyl, haloketoalkenyl, haloalkylaryl, haloalkyl heteroaryl, wherein one or more non-adjacent CH$_2$ groups can be replaced independently of one another by —O—, —S—, —NH—, —NR$^{\circ\circ\circ}$—, —SiR$^\circ$R$^{\circ\circ}$—, —CO—, —COO—, —COR$^\circ$OR$^{\circ\circ}$—, —OCO—, —OCO—O—, —SO$_2$—, —S—CO—, —CO—S—, —O—CS—, —CS—O—, —CY1=CY2 or —C≡C— in such a way that O and/or S atoms are not directly connected to one another, likewise optionally substituted with aryl or heteroaryl.

2. The component according to claim 1, wherein R$^3$ is selected from the group consisting of haloalkyl, halogenaryl, at least partially halogenated long-chain alkyl, halogencycloalkyl, haloheteroaryl, haloalkylaryl and haloalkyl heteroaryl.

3. The component according to claim 1, wherein R$^3$ is a perfluorinated hydrocarbon radical.

4. The component according to claim 1, wherein R$^3$ has the following general formula:

*—(CF$_2$)$_n$CF$_3$ wherein n can assume the values from 0 to 19.

5. The component according to claim 1, wherein R$^3$ is selected from the group consisting of:

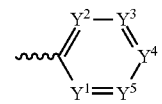

wherein Y$^1$-Y$^5$ are selected independently of one another from the group consisting of: C—H, C-D, C—F, C—NO$_2$, C—CN, C-halogen, C-pseudohalogen, N or C—C$_n$F$_{2n+1}$, where n=1 to 10.

6. An organic electronic component having a zinc complex as a p-type dopant in charge carrier generation layers containing a zinc atom and at least one ligand L of the following structure:

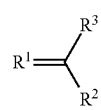

herein R$^1$ and R$^2$ are, independently of one another, oxygen, sulfur, selenium, NH or NR$^4$, wherein R$^1$ and/or R$^2$ are coordinated to the zinc atom, wherein R$^4$ is selected from the group consisting of alkyl or aryl and can be connected to R$^3$; and R$^3$ is selected from the group consisting of alkyl, long-chain alkyl, cycloalkyl, haloalkyl, at least partially halogenated long-chain alkyl, halocycloalkyl, aryl, arylenes, haloaryl, heteroaryl, heteroarylenes, heterocycloalkylenes, heterocycloalkyl, halogen-heteroaryl, alkenyl, haloalkenyl, alkinyl, haloalkinyl, ketoaryl, haloketoaryl, ketoheteroaryl, ketoalkyl, haloketoalkyl, ketoalkenyl, haloketoalkenyl, haloalkylaryl, haloalkyl heteroaryl, wherein one or more non-adjacent CH$_2$ groups can be replaced independently of one another by —O—, —S—, —NH—, —NR$^{\circ\circ\circ}$—, —SiR$^\circ$R$^{\circ\circ}$—, —CO—, —COO—, —COR$^\circ$OR$^{\circ\circ}$—, —OCO—, —OCO—O—, —SO$_2$—, —S—CO—, —CO—S—, —O—CS—, —CS—O—, —CY1=CY2 or —C≡C— in such a way that O and/or S atoms are not directly connected to one another, likewise optionally substituted with aryl or heteroaryl.

7. The component according to claim 1, wherein the organic p-doped region comprises an organic hole-conducting matrix, into which the p-type dopant is introduced.

8. The component according to claim 1, wherein the proportion of the zinc complex relative to the p-doped region is ≥0.1% by volume to ≤50% by volume.

9. The component according to claim 1, wherein the charge carrier generation layer additionally has an n-conducting region.

10. The component according to claim 9, wherein an intermediate region is arranged between the n-conducting region and the organic p-doped region.

11. The component according to claim 10, wherein the intermediate region is designed as an intermediate layer and has a thickness of 0.5 nm to 10 nm.

12. The component according to claim 1, wherein the n-conducting region has a common interface with the organic p-doped region.

13. The component according to claim 9, wherein the n-conducting region is an organic n-doped region.

14. The component according to claim 13, wherein the organic n-doped region has an organic electron-conducting matrix into which an n-type dopant is introduced.

15. The component according to claim 1, further comprising
an anode,
a first emitter layer
a second emitter layer
a cathode,
wherein the charge carrier generation layer is arranged between the first and second emitter layers.

16. The component according to claim 15, comprising at least one further charge carrier generation layer and at least one further emitter layer.

17. The component according to claim 6, wherein both R$^1$ and R$^2$ are oxygen.

18. An organic electronic component according to claim 6, in the p-doped region of a charge carrier generation layer.

19. An organic electronic component having
at least one charge carrier generation layer which has an organic p-doped region containing a zinc complex as the p-dopant, wherein the zinc complex comprises a zinc atom and at least one ligand L of the following structure:

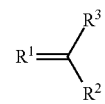

wherein R$^1$ and R$^2$ are, independently of one another, oxygen, sulfur, selenium, NH or NR$^4$, wherein R$^1$ and/or R$^2$ are coordinated to the zinc atom, wherein R$^4$ is selected from the group consisting of alkyl or aryl and can be connected to R$^3$; and R$^3$ is selected from the group consisting of alkyl, long-chain alkyl, cycloalkyl, haloalkyl, at least partially halogenated long-chain alkyl, halocycloalkyl, aryl, arylenes, haloaryl, heteroaryl, heteroarylenes, heterocycloalkylenes, heterocycloalkyl, halogen-heteroaryl, alkenyl, haloalkenyl, alkinyl, haloalkinyl, ketoaryl, haloketoaryl, ketoheteroaryl, ketoalkyl, haloketoalkyl, ketoalkenyl, haloketoalkenyl, haloalkylaryl, haloalkyl heteroaryl, wherein one or more non-adjacent CH$_2$ groups can be replaced independently of one another by —O—, —S—, —NH—, —NR$^{\circ\circ\circ}$—, —SiR$^\circ$R$^{\circ\circ}$—, —CO—, —COO—, —COR$^\circ$OR$^{\circ\circ}$—, —OCO—, —OCO—O—, —SO$_2$—, —S—CO—, —CO—S—, —O—CS—, —CS—O—, —CY1=CY2 or —C≡C— in such a way that O and/or S atoms are not directly connected to one another, likewise optionally substituted with aryl or heteroaryl.

20. The component according to claim 1, wherein one or more non-adjacent CH$_2$ groups are substituted with aryl or heteroaryl, wherein the aryl or heteroaryl contain 1 to 30 C atoms.

* * * * *